United States Patent
Yung et al.

(10) Patent No.: US 10,619,135 B2
(45) Date of Patent: *Apr. 14, 2020

(54) GROWTH FACTOR-FREE PROLIFERATION AND DIFFERENTIATION OF NEURAL STEM CELLS ON INORGANIC EXTRACELLULAR NANOMATRICES

(71) Applicant: Hong Kong Baptist University, Hong Kong (HK)

(72) Inventors: Kin Lam Yung, Hong Kong (HK); Zhifeng Huang, Hong Kong (HK); Nga Ping Lui, Hong Kong (HK)

(73) Assignee: Hong Kong Baptist University, Hong Kong (HK)

( * ) Notice: Subject to any disclaimer, the term of this patent is extended or adjusted under 35 U.S.C. 154(b) by 109 days.

This patent is subject to a terminal disclaimer.

(21) Appl. No.: 15/600,808

(22) Filed: May 22, 2017

(65) Prior Publication Data

US 2017/0335279 A1 Nov. 23, 2017

Related U.S. Application Data

(60) Provisional application No. 62/340,500, filed on May 23, 2016.

(51) Int. Cl.
| | |
|---|---|
| *C01B 33/18* | (2006.01) |
| *C12N 5/0797* | (2010.01) |
| *C01G 23/04* | (2006.01) |
| *C01G 23/047* | (2006.01) |
| *B82Y 30/00* | (2011.01) |

(Continued)

(52) U.S. Cl.
CPC .......... *C12N 5/0623* (2013.01); *C01B 33/18* (2013.01); *C01G 23/043* (2013.01); *C01G 23/047* (2013.01); *B82Y 5/00* (2013.01); *B82Y 30/00* (2013.01); *B82Y 40/00* (2013.01); *C01P 2004/16* (2013.01); *C12N 2533/00* (2013.01); *C12N 2535/00* (2013.01); *Y10S 977/766* (2013.01); *Y10S 977/768* (2013.01); *Y10S 977/891* (2013.01); *Y10S 977/923* (2013.01)

(58) Field of Classification Search
CPC ................ C12N 5/0623; C12N 5/0797; C12N 2533/00; C12N 2535/00; C01G 23/047; C01G 23/04; C01G 23/043; Y10S 977/766; Y10S 977/768; Y10S 977/891; Y10S 977/923; B82Y 5/00; B82Y 30/00; B82Y 40/00; C01B 33/18; C01P 2004/16
See application file for complete search history.

(56) References Cited

FOREIGN PATENT DOCUMENTS

| | | |
|---|---|---|
| CN | 101638238 A | 2/2010 |
| CN | 103276449 A | 9/2013 |
| WO | 2011100638 A1 | 8/2011 |

OTHER PUBLICATIONS

Huang et al (NPL: "Wafter-scale, three-dimensional porous thin films deposited at glancing angle", Nanoscale, 2014, 6 pages 9401-9409, refer to as Huang 2).*

(Continued)

*Primary Examiner* — Smita S Patel
(74) *Attorney, Agent, or Firm* — Idea Intellectual Limited; Margaret A. Burke; Sam T. Yip

(57) ABSTRACT

The present invention provides nanostructures for use in proliferation and differentiation of neural stem cells. The present invention also provides method of proliferating and differentiating neural stem cells.

12 Claims, 25 Drawing Sheets

(51) Int. Cl.
B82Y 5/00 (2011.01)
B82Y 40/00 (2011.01)

(56) References Cited

OTHER PUBLICATIONS

Huang et al (NPL: Morphology Control of Nanotube Arrays, Advanced Materials, 2009, 21 pages 2983-2987, refer to as Huang 1.*
CN 10326449, Dong et al, see machine translation, 2013.*
Bosi, S. et. al., "From 2D to 3D: Novel Nanostructured Scaffolds to Investigate Signalling in Reconstructed Neuronal Networks", Scientific Reports,2015, 5, 9562, p. 1-11.
Eroshenko, N. et. al., "Effect of Substrate Stiffness on Early Human Embryonic Stem Cell Differentiation", Journal of Biological Engineering, 2013, 7 (1), 7, p. 1-8.
Macri-Pellizzeri, L. et. al., "Substrate Stiffness and Composition Specifically Direct Differentiation of Induced Pluripotent Stem Cells", Tissue Engineering Part A, 2015, 21 (9-10), 1633-1641, p. 1-39.
Saha, K. et. al., "Substrate Modulus Directs Neural Stem Cell Behavior", Biophysical Journal, 2008, 95 (9), p. 4426-4438.
Huebsch, N. et. al., "Harnessing Traction-Mediated Manipulation of the Cell-Matrix Interface to Control Stem-Cell Fate", Nat. Mater., 2010, 9 (6), 518-526, p. 1-19.
Bizen, N. et. al., "A Growth-Promoting Signaling Component Cyclin D1 in Neural Stem Cells Has Antiastrogliogenic Function to Execute Self-Renewal", Stem Cells, 2014, 32(6), p. 1602-1615.
Takase, N. et. al., "NCAM- and FGF-2-mediated FGFR1 Signaling in the Tumor Microenvironment of Esophageal Cancer Regulates the Survival and Migration of Tumor-Associated Macrophages and Cancer Cells", Cancer Lett, 2016, 380(1), p. 47-58.
Guan, X. M., "Cancer Metastases: Challenges and Opportunities", Acta Pharm Sin B, 2015, 5 (5), p. 402-418.
Sexena, N. K. et. al., "Multifaceted Leptin Network: The Molecular Connection Between Obesity and Breast Cancer", J Mammary Gland Biol, 2013, 18 (0), p. 309-320.
Strand, B. L. et. al., "Alginate-Polylysine-Alginate Microcapsules: Effect of Size Reduction on Capsule Properties", J Microencapsulation, 2002, 19 (5), p. 615-630.
Ge, H. F. et. al., "Poly-L-Ornithine Promotes Preferred Differentiation of Neural Stem/Progenitor Cells via ERK Signalling Pathway", Scientific Reports, 2015, 5, 15535, p. 1-10.
Spenle, C. et. al., "The Laminin Response in Inflammatory Bowel Disease: Protection or Malignancy?", Plos One, 2014, 9 (10), e111336, p. 1-10.
Sun, T. et. al., "A Comparison of Proliferative Capacity and Passaging Potential Between Neural Stem and Progenitor Cells in Adherent and Neurosphere Cultures", Int J Dev Neurosci, 2011, 29 (7), p. 723-731.
Ma, Q. et. al., "Three-Dimensional Stiff Graphene Scaffold on Neural Stem Cells Behavior", ACS Applied Materials & Interfaces, 2016, 8 (50), p. 34227-34233.
Moe, A. A. K. et. al., "Microarray with Micro- and Nano-topographies Enables Identification of the Optimal Topography for Directing the Differentiation of Primary Murine Neural Progenitor Cells", Small, 2012, p. 1-12.
Dalby, M. J. et. al., "The Control of Human Mesenchymal Cell Differentiation Using Nanoscale Symmetry and Disorder", Nature Materials, 2007, 6 (12), p. 997-1003.
Jan, E. et. al., "Successful Differentiation of Mouse Neural Stem Cells on Layer-by-Layer Assembled Single-Walled Carbon Nanotube Composite", Nano Letters, 2007, 7 (5), p. 1123-1128.
Das, R. K. et. al., "A Review of the Effects of the Cell Environment Physicochemical Nanoarchitecture on Stem Cell Commitment", Biomaterials, 2014, 35 (20), p. 5278-5293.
Mendes, P. M., "Cellular Nanotechnology: Making Biological Interfaces Smarter", Chemical Society Reviews, 2013, 42 (24), p. 9207-9218.
Dado, D. et. al., "Mechanical Control of Stem Cell Differentiation", Regen Med, 2012, 7 (1), p. 101-116.
Abbasi, N. et. al., "Influence of Oriented Nanofibrous PCL Scaffolds on Quantitative Gene Expression During Neural Differentiation of Mouse Embryonic Stem Cells", Journal of Biomedical Materials Research A, 2016, 104A (1), p. 155-164.
Dingal, P. C. D. P. et. al., "Material Control of Stem Cell Differentiation: Challenges in Nano-Characterization", Current Opinion in Biotechnology, 2014, 28, p. 46-50.
Leipzig, N. D. et. al., "The Effect of Substrate Stiffness on Adult Neural Stem Cell Behavior", Biomaterials, 2009, 30 (36), p. 6867-6878.
Fu, J. P. et. al., "Mechanical Regulation of Cell Function with Geometrically Modulated Elastomeric Substrates", Nature Methods, 2010, 7 (9), p. 733-736.
Zouani, O. F. et. al., "Effect of BMP-2 from Matrices of Different Stiffnesses for the Modulation of Stem Cell Fate", Biomaterials, 2013, 34 (9), p. 2157-2166.
Wen, J. H. et. al., "Interplay of Matrix Stiffness and Protein Tethering in Stem Cell Differentiation", Nat. Mater., 2014, 13 (10), p. 979-987.
Gautrot, J. E et. al., "The Nanoscale Geometrical Maturation of Focal Adhesions Controls Stem Cell Differentiation and Mechanotransduction", Nano Letters, 2014, 14 (7), p. A-H.
Ye, K. et. al., "Matrix Stiffness and Nanoscale Spatial Organization of Cell-Adhesive Ligands Direct Stem Cell Fate", Nano Letters, 2015, 15 (7), p. A-J.
Oh, S. et. al., "Significantly Accelerated Osteoblast Cell Growth on Aligned TiO2 Nanotubes", Journal of Biomedical Materials Research A, 2006, 78 (1), p. 97-103.
Park, J. et. al., "Nanosize and Vitality: TiO2 Nanotube Diameter Directs Cell Fate", Nano Letters, 2007, 7 (6), p. 1686-1691.
Yim, E. K. F. et. al., "Synthetic Nanostructures Inducing Differentiation of Human Mesenchymal Stem Cells into Neuronal Lineage", Exp Cell Res, 2007, 313 (9), p. 1820-1829.
Oh, S. et. al., "Stem Cell Fate Dictated Solely by Altered Nanotube Dimension", Proceedings of the National Academy of Sciences of the United States of America, 2009, 106 (7), p. 2130-2135.
Kilian, K. A. et.al., "Geometric Cues for Directing the Differentiation of Mesenchymal Stem Cells", Proceedings of the National Academy of Sciences of the United States of America, 2010, 107 (11), p. 4872-4877.
Tay, C. Y. et. al., "Micropatterned Matrix Directs Differentiation of Human Mesenchymal Stem Cells towards Myocardial Lineage", Experimental Cell Research, 2010, 316 (7), p. 1159-1168.
Bucaro, M. A. et. al., "Fine-Tuning the Degree of Stem Cell Polarization and Alignment on Ordered Arrays of High-Aspect-Ratio Nanopillars", ACS Nano, 2012, 6 (7), p. 6222-6230.
Zouani, O. F. et. al., "Altered Nanofeature Size Dictates Stem Cell Differentiation", Journal of Cell Science, 2012, 125 (5), p. 1217-1224.
Ding, J. et. al., "Fabrication of RGD Micro-Nanopattern and Corresponding Study of Stem Cell Differentiation", Nano Letters, 2015, 15 (3), p. 1-30.
Thorpe, A. A. et. al., "Thermally Triggered Hydrogel Injection into Bovine Intervertebral Disc Tissue Explants Induces Differentiation of Mesenchymal Stem Cells and Restores Mechanical Function", Acta Biomaterials, 2017, p. 212-226.
Greiner, A. M. et. al., "Nano- and Microstructured Materials for in Vitro Studies of the Physiology of Vascular Cells", Beilstein Journal of Nanotechnology, 2016, 7, p. 1620-1641.
Liu, J. J. et. al.,"Chiroptically Active Plasmonic Nanoparticles Having Hidden Helicity and Reversible Aqueous Solvent Effect on Chiroptical Activity", Small, 2016, 12 (42), p. 1-8.
Deng, J. H. et. al., "Radiative Loss-Determined Circular Dichroism of Plasmonic Nanospirals with Bendable Stability of Chiroptical Activity", Royal Society of Chemistry Advances, 2016, 6 (87), p. 84348-84353.
Huang, Z. F. et. al., "Wafer-Scale, Three-Dimensional Helical Porous Thin Films Deposited at a Glancing Angle", Nanoscale, 2014, 6 (16), p. 9401-9409.
Huang, Z. F. et. al., "Morphology Control of Nanotube Arrays", Advanced Materials, 2009, 21, p. 2983-2987.

(56) References Cited

OTHER PUBLICATIONS

Moyen, E. el. al., "Nanostructured Conducting Polymers for Stiffness Controlled Cell Adhesion", Nanotechnology, 2016, 27(7), 074001. p. 1-8.

Logan, T. T. et. al., "Runx1 Promotes Proliferation and Neuronal Differentiation in Adult Mouse Neurosphere Cultures", Stem Cell Research, 2015, 15 (3), p. 554-564.

Malik, A. et. al., "Development of Circadian Oscillators in Neurosphere Cultures during Adult Neurogenesis", Plos One, 2015, 10 (3), e0122937. p. 1-18.

Fan, Y. P. et. al., "Regionally-Specified Second Trimester Fetal Neural Stem Cells Reveals Differential Neurogenic Programming", Plos One, 2014, 9 (9), e105985. p. 1-12.

Binder, E. et. al., "Enteric Neurospheres Are Not Specific to Neural Crest Cultures: Implications for Neural Stem Cell Therapies", Plos One, 2015, 10 (3), e0119467, p. 1-18.

Fu, J. P. et. al., "Elimination of the Geomagnetic Field Stimulates the Proliferation of Mouse Neural Progenitor and Stem Cells", Protein Cell, 2016, 7 (9), p. 624-637.

Murai, K. et. al., "The TLX-miR-219 Cascade Regulates Neural Stem Cell Proliferation in Neurodevelopment and Schizophrenia iPSC model", Nature Communications, 2016, 7, 10965, p. 1-15.

Baral, S. et. al., "Effects of Gastrodiae Rhizoma on Proliferation and Differentiation of Human Embryonic Neural Stem Cells", Asian Pacific Journal of Tropical Medicine, 2015, 8 (10), P. 792-797.

Mitra, G. et. al., "MAP2c Prevents Arachidonic Acid-Induced Fibril Formation of Tau: Role of Chaperone Activity and Phosphorylation", Biophysical Chemistry, 2015, 205, p. 16-23.

Fazeli, Z. et. al., "Expression Pattern of Neuronal Markers in PB-MSCs Treated by Growth Factors Noggin, bFGF and EGF", Int J Mol Cell Med, 2015, 4 (4), p. 209-217.

McBeath, R. et. al., "Cell Shape, Cytoskelelal Tension, and RhoA Regulate Stem Cell Lineage Commitment", Developmental Cell, 2004, 6 (4),P. 483-495.

Yang, K. et al., "Nanotopographical Manipulation of Focal Adhesion Formation for Enhanced Differentiation of Human Neural Stem Cells", ACS Applied Materials Interfaces, 2013, 5 (21), p. 10529-10540.

International search report of PCT/CN2017/085447 dated Aug. 17, 2017.

European Search Report of corresponding European Patent Application No. 17802132.5 dated Nov. 21, 2019.

Zhifeng Huang et al., "Wafer-scale, three-dimensional helical porous thin films deposited at a glancing angle", Nanoscale, 2014, vol. 6, No. 16, pp. 9401-9409.

Hyunah Kwon et al., "Three-Dimensional Metal-Oxide Nanohelix Arrays Fabricated by Oblique Angle Deposition: Fabrication, Properties, and Applications", Nanoscale Research Letters, 2015, vol. 10, No. 1, p. 1-12.

Linxin Hu et al., "Fabrication of Optical Tunable Helical Thin Films", Journal of Materials Science & Technology, 2012, vol. 28, No. 2, pp. 97-102.

Shiqing Zhang et al., "Extracellular Nanomatrix-Induced Self-Organization of Neural Stem Cells into Miniature Substantia Nigra-Like Structures with Therapeutic Effects on Parkinsonian Rats", Advanced Science, 2019, pp. 1901822.

\* cited by examiner

V: Vertical

Z: Zigzag

R: Right Helix

L: Left Helix

GROWTH FACTOR-FREE PROLIFERATION AND DIFFERENTIATION OF NEURAL STEM CELLS ON INORGANIC EXTRACELLULAR NANOMATRICES

CROSS-REFERENCE TO RELATED APPLICATIONS

This application claims priority from U.S. Provisional Patent Application Ser. No. 62/340,500 filed on May 23, 2016, the disclosure of which is hereby incorporated by reference.

FIELD OF INVENTION

This invention is in the field of biotechnology and medical industries. In particular, this invention relates to method and substrates for differentiation of neural stem cells without the use of chemical growth factors.

BACKGROUND OF INVENTION

In recent years stem cell therapies have been developed and progress extremely fast in biomedical sciences. It will be hope for treating neurodegenerative diseases, such as Alzheimer's disease, Parkinson's disease and even stroke. During stem cell therapies, cell culture technology is used. Chemical growth factors (GFs) must be employed in order to induce stem cell proliferation and cell differentiation. Many of these growth factors are the same growth factors that can promote growth of cancer cells and cancer metastasis. Therefore, there are urgent needs to develop methods to induce in vitro stem cell proliferation and differentiation without using chemical growth factors.

Objective of the present invention is to provide methods and physical substrates for proliferation and differentiation of neural stem cells by means of physical structures without the need of using chemical growth factors.

To the best of the inventors' knowledge, the present invention disclosed herein is novel and inventive over the state of art.

Citation or identification of any reference in this section or any other section of this application shall not be construed as an admission that such reference is available as prior art for the present application.

SUMMARY OF INVENTION

The present invention is in the field of biotechnology and medical industries. In particular, this invention relates to methods and substrates for cell differentiation of neural stem cells. In one embodiment of the present invention, there is provided methods and substrates for differentiation of neural stem cells by means of physical structures without the need of using growth factors.

In a first aspect of the present invention, there is provided a nanostructure comprising a plurality of nanohelices or nanozigzags, wherein the plurality of nanohelices or nanozigzags are made of materials comprising $SiO_2$ or $TiO_x$ wherein x is in the range of $0.33 \leq x \leq 2$.

In a second embodiment of the first aspect of the present invention, there is provided a nanostructure comprising a plurality of nanohelices or nanozigzags, wherein said stem cells are neural stem cells.

In a first embodiment of the first aspect of the present invention, there is provided a nanostructure comprising a plurality of nanohelices or nanozigzags, wherein length of each nanohelix is at least 540 nm, each nanohelix comprises at least two pitches and having a helical pitch of at least 240 nm.

In a second embodiment of the first aspect of the present invention, there is provided a nanostructure comprising a plurality of nanohelices or nanozigzags, wherein the length of each nanozigzag is at least 550 nm, each nanozigzag comprises at least three pitches and having a pitch of at least 165 nm.

In a third embodiment of the first aspect of the present invention, there is provided a nanostructure comprising a plurality of nanohelices or nanozigzags, wherein the $SiO_2$ nanohelices have a stiffness of $12.6 \pm 1.8$ μN/nm.

In a fourth embodiment of the first aspect of the present invention, there is provided a nanostructure comprising a plurality of nanohelices or nanozigzags, wherein the $SiO_2$ nanozigzags have a stiffness of $19.7 \pm 2.3$ μN/nm.

In a fifth embodiment of the first aspect of the present invention, there is provided a nanostructure comprising a plurality of nanohelices or nanozigzags, wherein said nanostructure is manufactured using the GLAD technique.

In a sixth embodiment of the first aspect of the present invention, there is provided a nanostructure comprising a plurality of nanohelices or nanozigzags, wherein the $TiO_x$, wherein x is in the range of $0.33 \leq x \leq 2$ and the nanostructure has a shape independent stiffness of no more than 26 μN/nm.

In a seventh embodiment of the first aspect of the present invention, there is provided a nanostructure comprising a plurality of nanohelices or nanozigzags, wherein the nanohelices are left-hand oriented or right-handed oriented.

In a second aspect of the present invention, there is provided a nanostructure for inducing proliferation and differentiation of stem cells in the absence of chemical growth factors, wherein said nanostructure is made out of materials comprising $SiO_2$.

In a first embodiment of the second aspect of the present invention, there is provided a nanostructure for inducing proliferation and differentiation of stem cells in the absence of chemical growth factors, wherein said nanostructure comprises a plurality of nanohelices or nanozigzags.

In a second embodiment of the second aspect of the present invention, there is provided a nanostructure for inducing proliferation and differentiation of stem cells in the absence of chemical growth factors, wherein said stem cells are neural stem cells.

In a third embodiment of the second aspect of the present invention, there is provided a nanostructure for inducing proliferation and differentiation of stem cells in the absence of chemical growth factors, wherein length of each nanohelix is at least 540 nm, each nanohelix comprises at least two pitches and having a pitch of at least 240 nm.

In a fourth embodiment of the second aspect of the present invention, there is provided a nanostructure for inducing proliferation and differentiation of stem cells in the absence of chemical growth factors, wherein length of each nanozigzags is at least 550 nm, each nanozigzag comprises at least three pitches and having a pitch of at least 165 nm.

In a fifth embodiment of the second aspect of the present invention, there is provided a nanostructure for inducing proliferation and differentiation of stem cells in the absence of chemical growth factors, wherein the $SiO_2$ nanohelices have a stiffness of $12.6 \pm 1.8$ μN/nm.

In a sixth embodiment of the second aspect of the present invention, there is provided a nanostructure for inducing proliferation and differentiation of stem cells in the absence of chemical growth factors, wherein the $SiO_2$ nanozigzags have a stiffness of $19.7 \pm 2.3$ μN/nm.

In a seventh embodiment of the second aspect of the present invention, there is provided a nanostructure for inducing proliferation and differentiation of stem cells in the absence of chemical growth factors, wherein said nanostructure is manufactured using the GLAD technique.

In a eighth embodiment of the second aspect of the present invention, there is provided a nanostructure for inducing proliferation and differentiation of stem cells in the absence of chemical growth factors, wherein the nanohelices are left-hand or right-hand oriented.

Features, integers, characteristics, compounds, chemical moieties or groups described in conjunction with a particular aspect, embodiment or example of the invention are to be understood to be applicable to any other aspect, embodiment or example described herein unless incompatible therewith.

Those skilled in the art will appreciate that the invention described herein is susceptible to variations and modifications other than those specifically described.

The invention includes all such variation and modifications. The invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF DRAWINGS

The above and other objects and features of the present invention will become apparent from the following description of the invention, when taken in conjunction with the accompanying drawings, in which.

DETAILED DESCRIPTION OF INVENTION

Figure 1A:
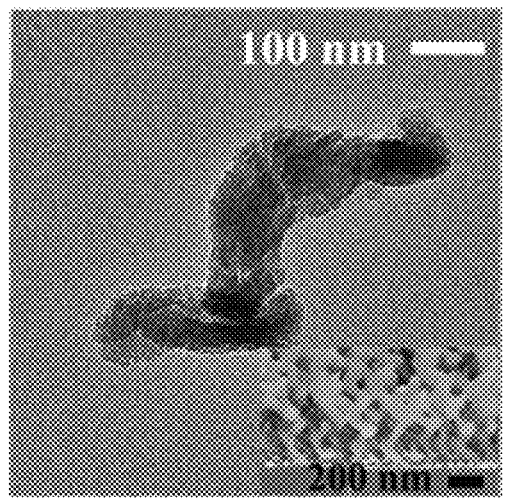
FIG. 1a shows TEM image of $SiO_2$ ECnM by GLAD having two-pitch left-handed nanohelices (NHs). Insets: cross-sectional SEM images of the ECnMs.

The present invention is not to be limited in scope by any of the specific embodiments described herein. The following embodiments are presented for exemplification only.

In recent years, stem cell therapies have been developed and made extremely fast progress in biomedical science. Neural stem cells (NSCs) are self-renewing and multipotent cells utilized for treating various neurodegenerative diseases. Chemical growth factors (GFs) are widely employed to induce stem cell proliferation and differentiation. Nowadays, in a commonly used NSC-culture method, "neurosphere assay", the growth of cells substantially relies on GFs; differentiated cells die in a few days and some undifferentiated cells can proliferate actively in respond to epidermal GFs and basic fibroblastic GFs to form neurospheres. However, GFs are potent to regulate cell-signaling pathways. If large amount of GFs is used to induce in vitro stem cells differentiation, it may cause a risk to develop cancer cells in vitro or tumors in vivo after transplantation. For example, fibroblast GF signaling, crucial for cell proliferation, survival and migration, plays an oncogenic role in many cancers; vascular epidermal GFs (an inducer of angiogenesis) and deregulated insulin GFs are related to the initiation and progression of cancer. Therefore, there is an urgent demand on developing new methods to induce in vitro NSC proliferation and differentiation without chemical GFs or additives.

The NSC-based therapies usually require extracellular matrices (ECMs) to vitro culture or receive additional treatment. ECMs can be made of organic scaffolds, such as poly-L-ornithine (PO), poly-L-Lysine (PLL), Laminin, and Fibronectin (FN). However, some studies suggest that PO and PLL could enhance the likelihood of host inflammatory responses, Laminin has a risk to be a carcinogenic substance, and FN would induce NSCs to lose their potentiality of proliferation after repeatedly passaged. The development of nanotechnology is penetrating biomedical sciences at a surprising speed, to devise a wide range of biocompatible/biodecomposable extracellular nanomatrices (ECnMs) to instruct the fate of stem cells in vitro. For instance, NSCs growing on stiff three-dimensional graphene foams exhibit enhanced differentiation; microarrays with nano-topographies enables the differentiation of primary murine neural progenitor cells, and disorder nanopatterns may favor stem cell lineage commitment compared to the order arrays; NSCs can successfully differentiate to neurons and astrocytes on carbon nanotubes. There are several aspects of the instructions to the fate of stem cells, which can be generally classified as biochemical and physiological cues. The biochemical cues stem from GFs, and the stem cell microenvironment of ECnMs is susceptible to multiple physiological cues, such as material, stiffness, and topography (including crystalline structure, geometric feature of nanostructures, fibrillar focal contact depth, pattern disorder, and pattern spacing). Purely mechanical support is provided to cells and some materials show no effects on cells viability. The topography cues can induce pronounced change in focal adhesion structures and alter the cytoskeleton and gene expression, to essentially influence cell attachment, migration, proliferation, and differentiation. As a result, an increasing attention has been focused on the nanotopography for its resemblance to in vitro environment. However, these studies were carried out with chemical GFs, to prevent solely studying the physiological cues. Novel biomaterials that mimic the physiological microenvironment for culturing and expanding NSCs without GFs or other additional biomaterials have attracted great interests to date. Rigidity and topographical control on ECnMs is a useful tool to understand, at both fundamental and application levels, how to encode instructions in the ECnMs for specialized cellular commitment and functions.

In the present invention, the inventors utilize the sculptured inorganic ECnMs, deposited by glancing angle deposition (GLAD), to induce GF-free NSCs proliferation and differentiation. The ECnMs of the present invention are made of biocompatible/biodegradable materials comprising $SiO_2$ or $TiO_2$, in the helices and zigzags having different topographies. The terms "ECnMs", "nanostructure" and "nano-matrices" are used interchangeably herein, which define the present invention for use in proliferation and differentiation of stem cells. The ECnMs of the present invention is made of inorganic oxides that proliferate the growth of NSCs, faster than induction by chemical GFs. The $SiO_2$ ECnMs of the present invention enables stem cells to differentiate to neuronal commitment. Both zigzag and helical nanostructure of the present invention enables stem cell differentiation. In a preferred embodiment, $SiO_2$ zigzag nanostructure mediates a better differentiation than the helical, which can be ascribed to physiological cues of topography and stiffness. In one embodiment of the present invention there is provided a GF-free method to minimize a risk of generating cancer cells for NSC therapies.

Figure 1B:
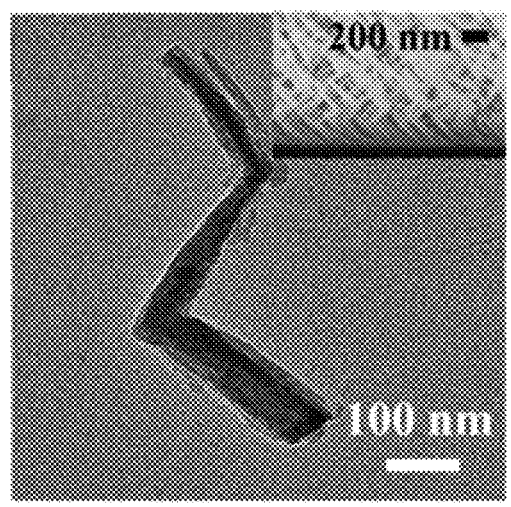
FIG. 1b shows TEM image of $SiO_2$ ECnM by GLAD having three-pitch nanozigzags (NZs). Insets: cross-sectional SEM images of the ECnMs.
Figure 1C:
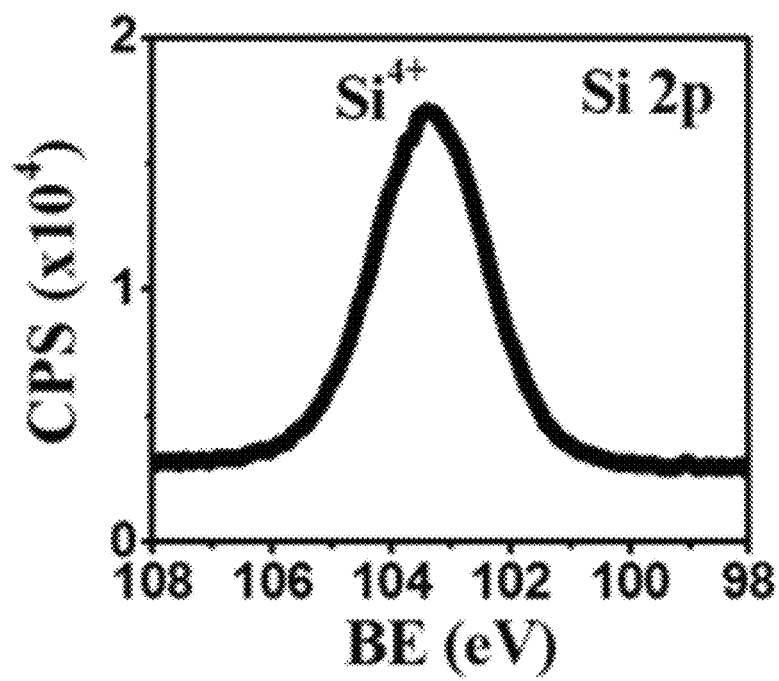
FIG. 1c shows XPS spectrum of NHs: Si2p for $SiO_2$ECnM by GLAD.
Figure 1D:
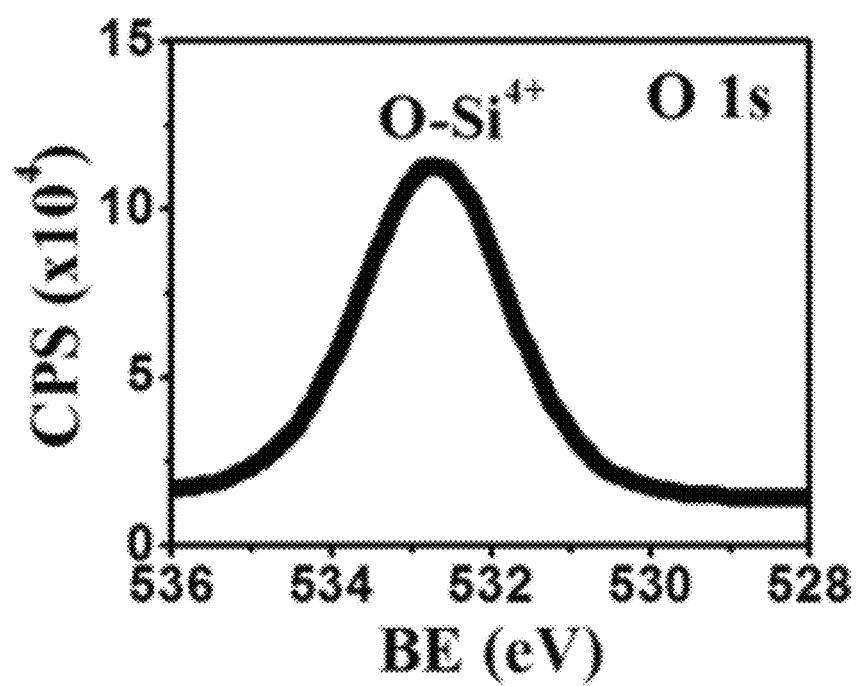
FIG. 1d shows XPS spectrum of NHs: O1s for $SiO_2$ECnM by GLAD.
Figure 1E:
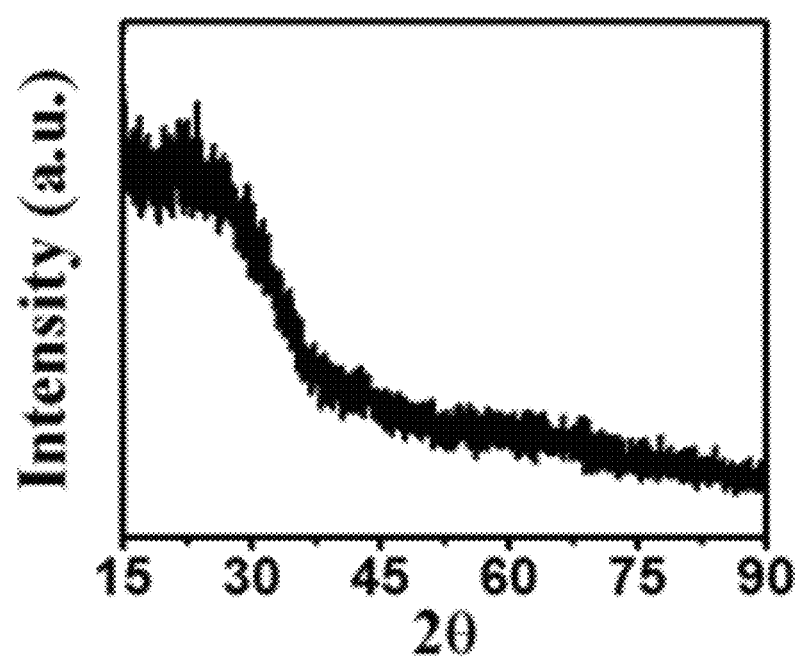
FIG. 1e shows XRD spectrum of $SiO_2$ ECnM NHs deposited on glass by GLAD.
Figure 2A:
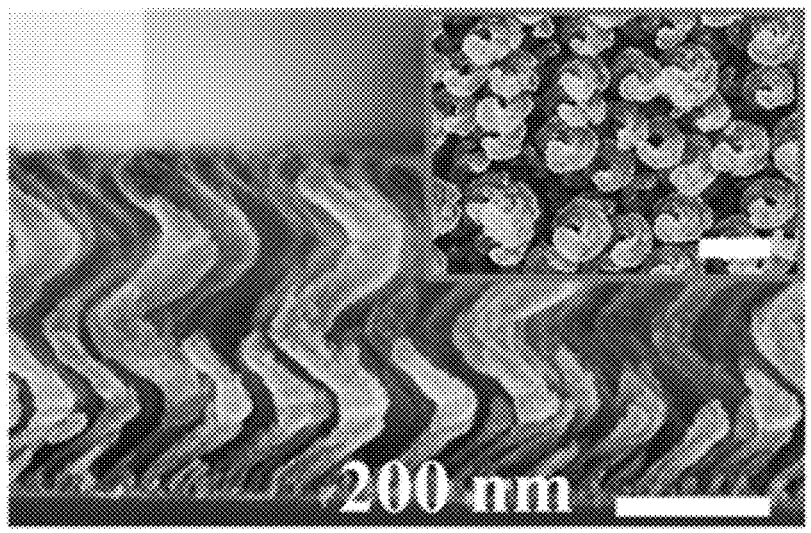
FIG. 2a shows cross sectional SEM images of left-handed NHs of $TiO_x$ ECnMs by GLAD. Insets shows top-down view of left-handed NHs $TiO_x$ ECnMs by GLAD (scale bars: 200 nm).
Figure 2B:
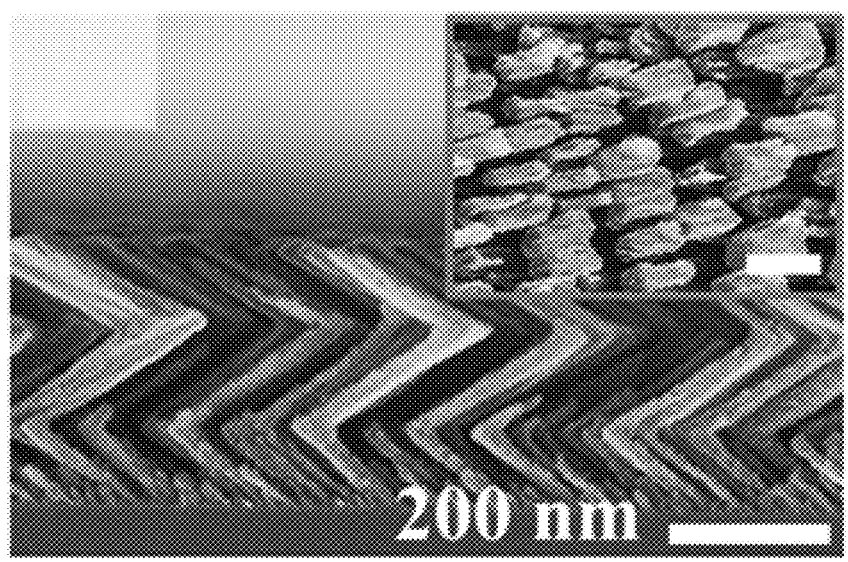
FIG. 2b shows cross sectional SEM images of NZs $TiO_x$ ECnMs by GLAD. Insets shows top-down view of NZs $TiO_x$ ECnMs by GLAD (scale bars: 200 nm).
Figure 2C:
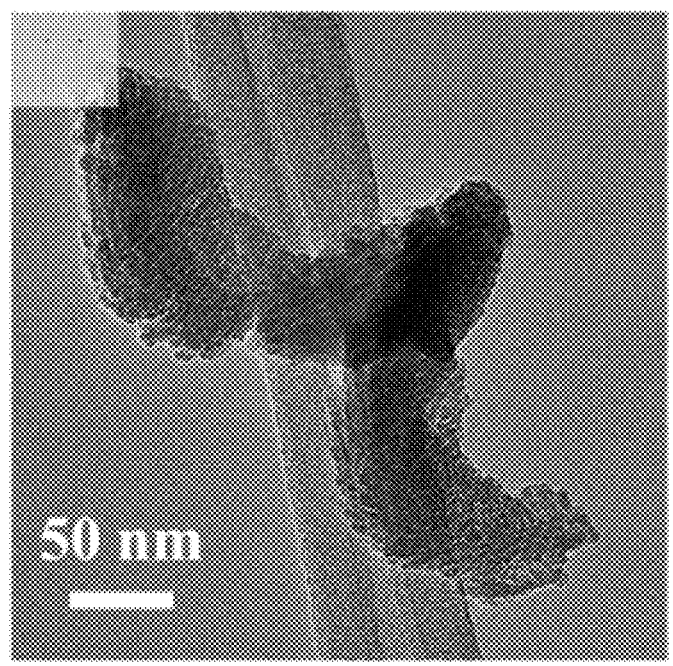
FIG. 2c shows TEM image of individual $TiO_x$ nanostructures of left-handed NHs $TiO_x$ ECnMs by GLAD.
Figure 2D:
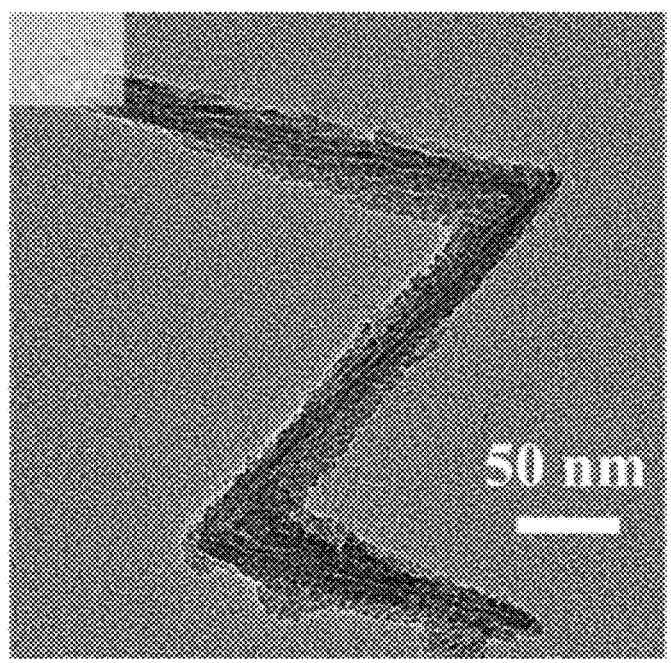
FIG. 2d shows TEM image of individual $TiO_x$ nanostructures of NZs $TiO_x$ ECnMs by GLAD.
Figure 11A:
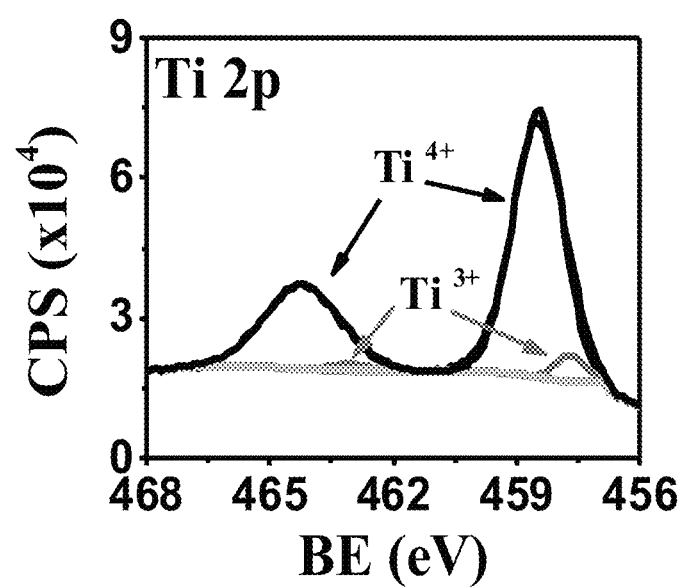
FIG. 11a shows XPS spectra of the $TiO_x$ NH ECnMs deposited on sapphire: Ti2p.
Figure 11B:
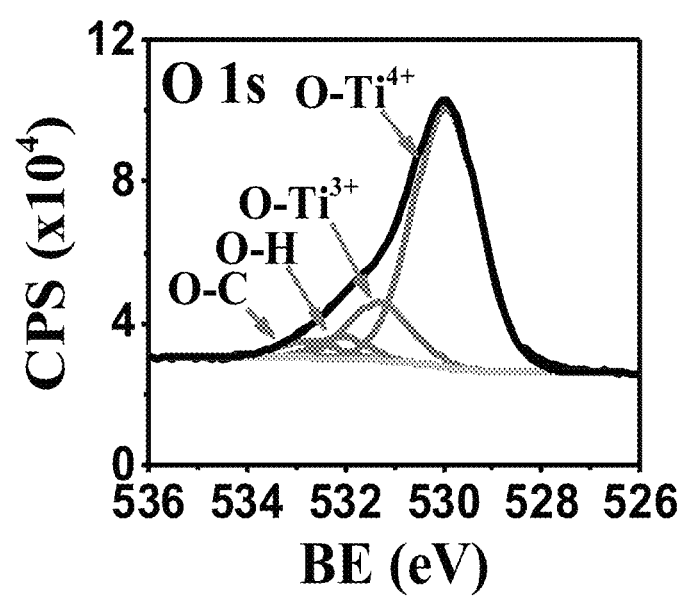
FIG. 11b shows XPS spectra of the $TiO_x$ NH ECnMs deposited on sapphire: O1s.
Figure 11C:
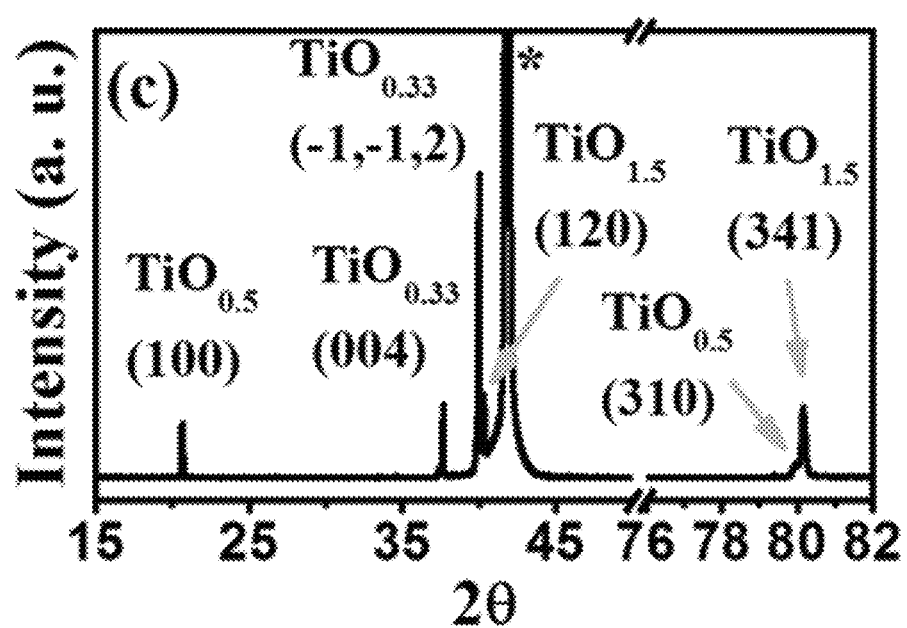
FIG. 11c shows XRD spectra of the $TiO_x$ NH ECnMs deposited on sapphire. The peak marked by asteroid is assigned to the sapphire.

GLAD is operated to deposit a close-packed silicon oxide ECnM sculptured in helix (left-handed nanohelices or NHs FIG. 1a) or zigzag (nanozigzags or NZs, FIG. 1b). The two nanostructures vertically grow along the direction of the substrate's surface normal. $Si^{4+}$ ions are mainly detected by XPS (FIGS. 1c, 1d), illustrating that the present nanostructure surfaces are composed of $SiO_2$. The present nanostructure is amorphous (FIG. 1e). The NZs have XPS and XRD spectra identical to those of the NHs, which aren't shown here. In one embodiment, the nanostructure comprises a plurality of SiO$_2$ nanohelices, length of each nanohelix (H) is at least 540 nm and each nanohelix comprises at least two pitches and having a helical pitch (P) of ~240 nm. In another embodiment, the nanostructure comprises a plurality of SiO$_2$ nanozigzags, length of each nanozigzag (H) is at least 550 nm and each nanozigzag comprises at least three pitches and a pitch (P) of ~165 nm (as summarized in Table 1) The helical pitch of a nanohelix or the pitch of a nanozigzag (P) herein is defined as the vertical distance separating two points on a helix or a zigzag in one complete helix turn or zigzag. n is the number of zigzags or complete helix turn in each nanozigzag or nanohelix. Length of each nanohelix/nanozigzag (H) is calculated from the formula: H=nP+d. The NHs have a surface rougher than the NZs (FIG. 1a versus 1b). Wire diameter (d) is herein defined as the diameter of the nanozigzag and nanohelix body. Wire diameter (d) of both nanostructures, especially for NZs, gradually widens along the growth direction, owing to the competition growth induced by the self-shadowing effect of GLAD. To show the dependence of the NSC proliferation and differentiation on different material of ECnMs, titanium oxides TiO$_x$ are deposited in NHs (FIGS. 2a, 2c) and NZs (FIGS. 2b, 2d) using GLAD. XPS spectra shows Ti$^{3+}$ and Ti$^{4+}$ ions are found on the nanostructure surfaces (FIGS. 11a, 11b) for TiO$_x$ NHs ECnM, where 1.5≤x≤2. XRD spectrum shows TiO$_x$, where 0.33≤x≤1.5 are found in the cores of the ECnM (FIG. 11c). No TiO$_2$ are detected on the nanostructure surfaces by XRD. This is likely due to the fact that the surface layers of TiO$_2$ are too thin to detect. It is illustrated that the core of ECnM is composed of TiO$_x$ with smaller x (0.33≤x≤1.5) and the shell or surface of ECnM is composed of TiO$_x$ with larger x (1.5≤x≤2), due to spontaneous oxidation on the surfaces prohibits further oxidation in the cores. The TiO$_x$ ECnMs appear to be shorter in length than the SiO$_2$ ECnMs sculptured in the same shape (Table 1), and have crystalline structures (FIG. 11c). Analogously, the TiO$_x$ NHs and NZs have the widening effect on d (FIGS. 2a, 2b) and rough surfaces (FIGS. 2c, 2d). SiO$_2$ has an electric conductivity lower than TiO$_x$, the SEM images of the SiO$_2$ ECnMs appear to be much more blurry than TiO$_x$ECnMs (insets of FIG. 1a, 1b versus FIGS. 2a, 2b). In one embodiment, the nanostructure comprises right-handed NHs made from SiO$_2$ or TiO$_x$. In another embodiment, the nanostructure comprises left-handed NHs (not shown here). In another embodiment, the nanostructure comprises right-handed and left-handed NHs.

Figure 3A:
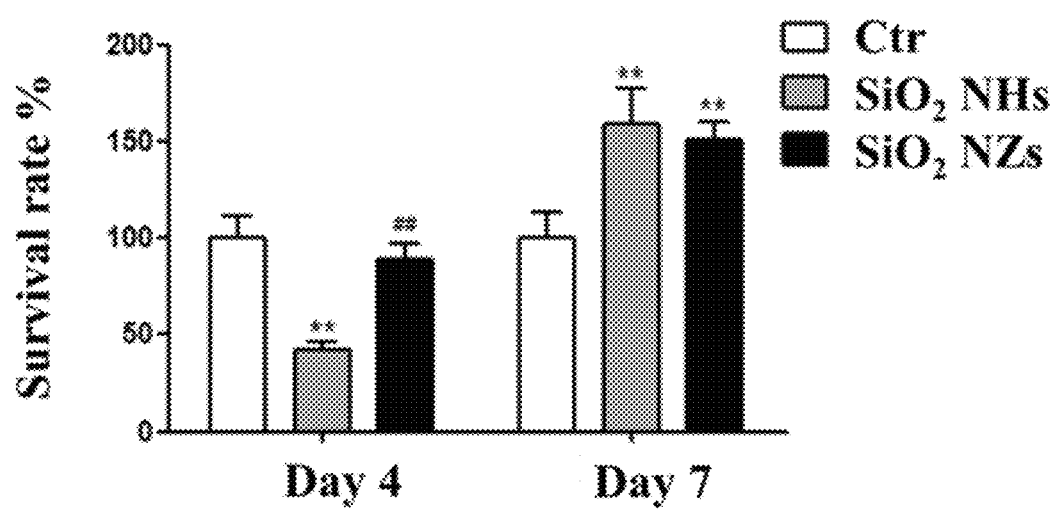
FIG. 3a shows survival rate on day 4 and day 7 of NSCs cultured on $SiO_2$ ECnMs in a shape of the helix (NHs) and zigzag (NZs). **$p<0.01$, compared with the control group (i.e., Ctr), ## $p<0.01$, compared with the NHs group.
Figure 3B:
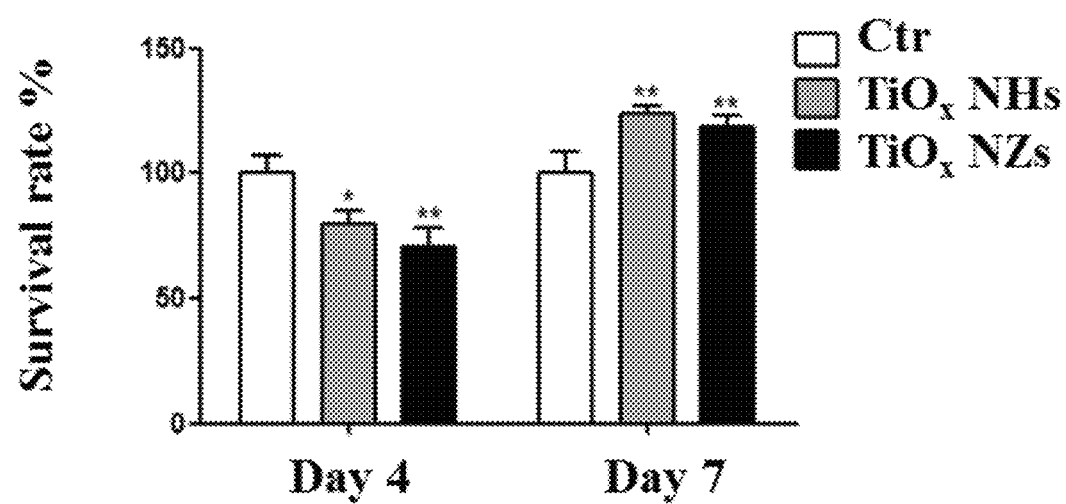
FIG. 3b shows survival rate of day 4 and day 7 of NSCs cultured on the $TiO_x$ ECnMs in a shape of the helix (NHs) and zigzag (NZs). *$p<0.05$, **$p<0.01$, compared with the control group.
Figure 5:
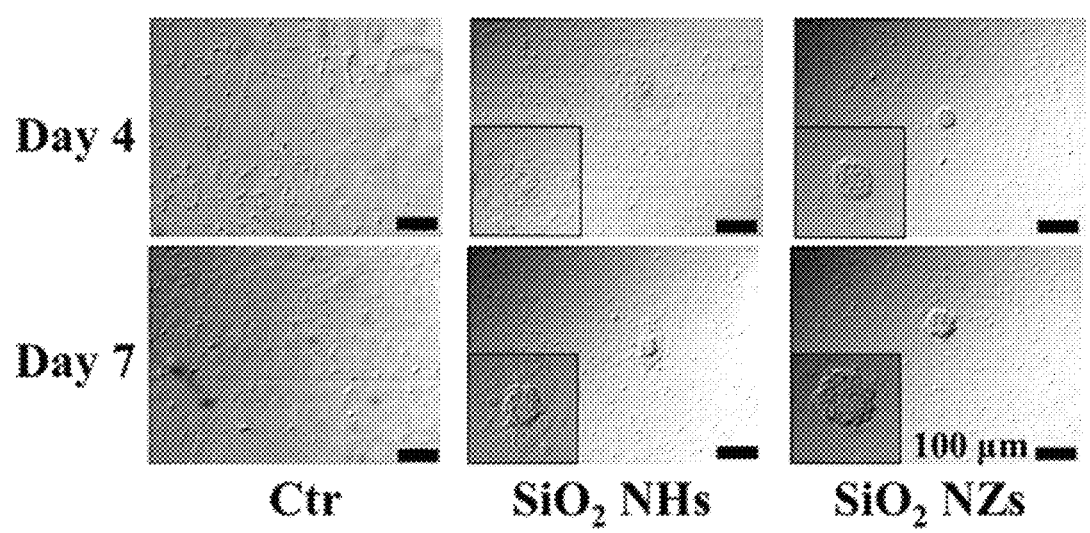
FIG. 5 shows microscopy images of neurosphere growth of NSCs having cultured on the $SiO_2$ ECnMs in a shape of the helix (NHs) or zigzag (NZs) for 4 and 7 days. Scale bar: 100 μm.
Figure 6:
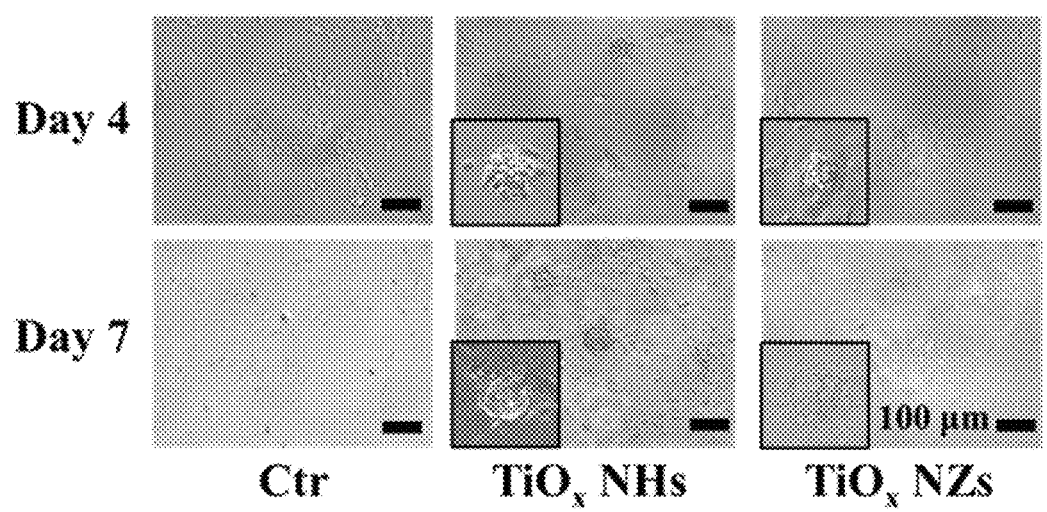
FIG. 6 shows microscopy images of neurosphere growth of NSCs having cultured on the $TiO_x$ ECnMs in a shape of the helix (NHs) or zigzag (NZs) for 4 and 7 days. Scale bar: 100 μm.

To show the proliferation of NSCs on ECnMs, MTT and neurosphere assay are performed after culturing NSCs on ECnMs for 4 and 7 days. Compared with the control group, the survival rate of NSCs on the SiO$_2$ and TiO$_x$ ECnMs decrease in day 4 but significantly increase on day 7 (FIGS. 2a and 3b). The change in survival rate of NSCs on ECnMs is ascribed to ability of ECnMs to promote proliferation of NSCs and to inhibit growth of other non-stem cells. This is further verified by studies below that show stiffness of nanostructure can control the eventual fate of non-stem cells. The degree of NSC proliferation on the helical and the zigzag structures are similar (FIGS. 2a and 3b). NHs and NZs made of SiO$_2$ or TiO$_x$ markedly promote the formation of neurospheres compared to the control group on day 4 and 7 (FIGS. 5 and 6). The neurospheres formed on day 4 have a diameter approximately larger than 50 μm. It is known in the art that neurospheres typically grow to have a diameter of 50 μm on day 5 in the presence of GFs. The inorganic ECnMs of the present invention accelerate proliferation of NSC and stimulate NSC in vitro viability without GFs.

Figure 7A:
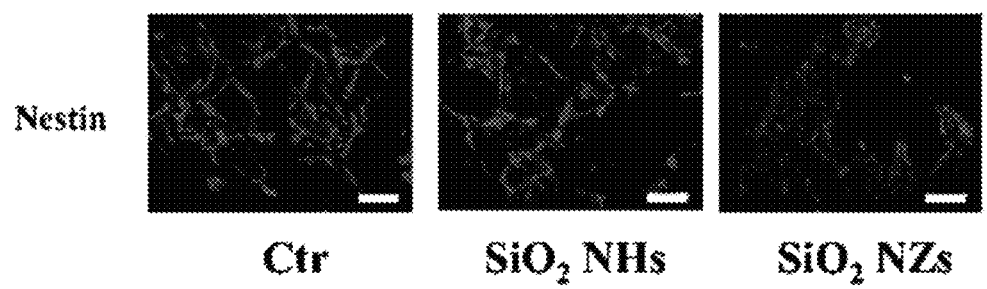
FIG. 7a shows fluorescence images of Nestin in NSC cultured on $SiO_2$ ECnMs in a shape of the helix (NHs) or zigzag (NZs). Scale bar: 50 μm.
Figure 8A:
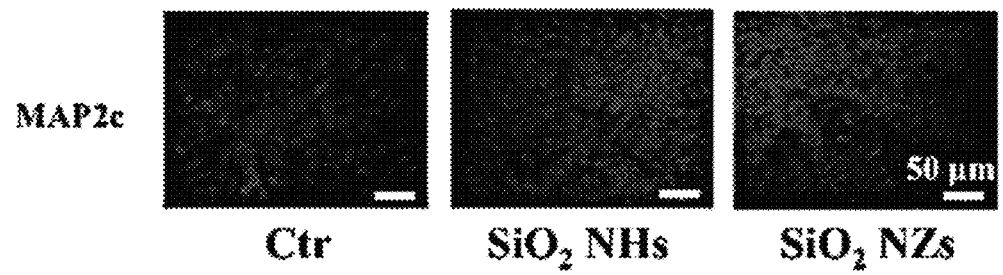
FIG. 8a shows fluorescence images of MAP2c in NSC cultured on the $SiO_2$ ECnMs in a shape of the helix (NHs) or zigzag (NZs). Scale bar: 50 μm.
Figure 9A:
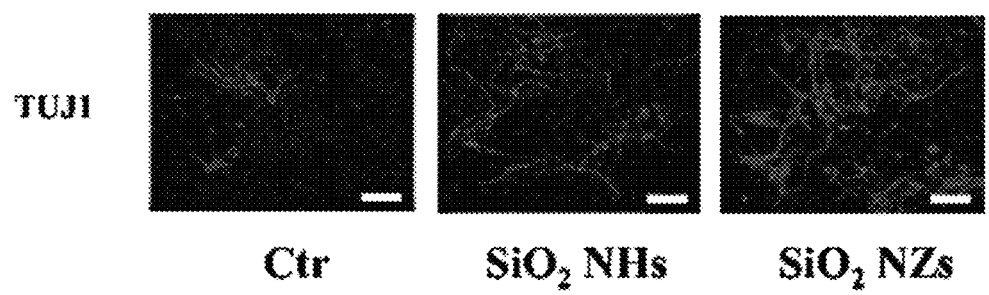
FIG. 9a shows fluorescence images of TUJ1 in NSC cultured on the $SiO_2$ ECnMs in a shape of the helix (NHs) or zigzag (NZs). Scale bar: 50 μm.
Figure 10A:
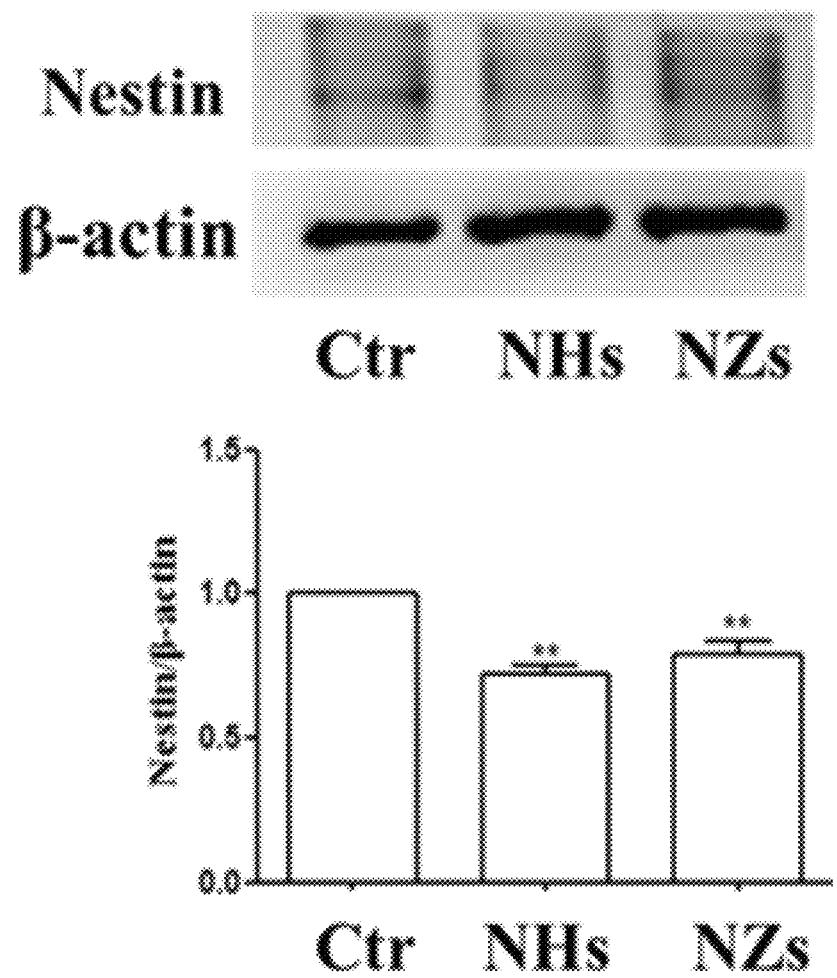
FIG. 10a shows western blot analysis of Nestin protein expression in NSC cultured on $SiO_2$ ECnMs in a shape of the helix (NHs) or zigzag (NZs) on day 4. **$p<0.01$ compared with the control group; # $p<0.05$, ## $p<0.01$ compared with the NHs group.
Figure 10B:
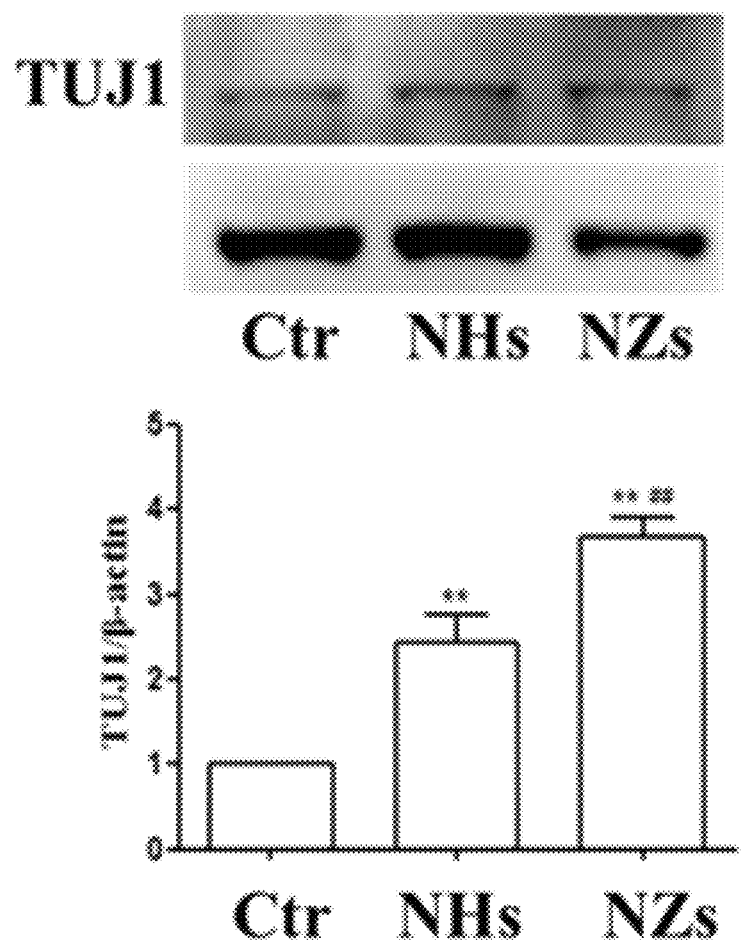
FIG. 10b shows western blot analysis of TUJ1 protein expression in NSC cultured on $SiO_2$ ECnMs in a shape of the helix (NHs) or zigzag (NZs) on day 7. **$p<0.01$ compared with the control group; # $p<0.05$, ## $p<0.01$ compared with the NHs group.
Figure 10C:
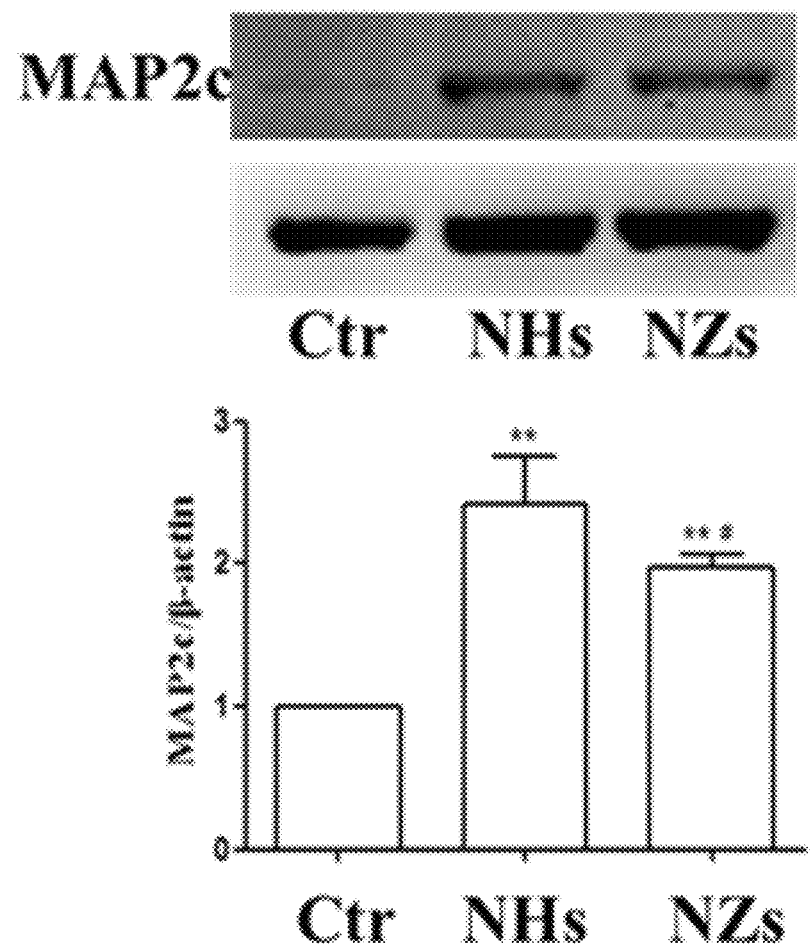
FIG. 10c shows western blot analysis of MAP2c protein expression in NSC cultured on $SiO_2$ ECnMs in a shape of the helix (NHs) or zigzag (NZs) on day 7. **p<0.01 compared with the control group; # p<0.05, ## p<0.01 compared with the NHs group.
Figure 10D:
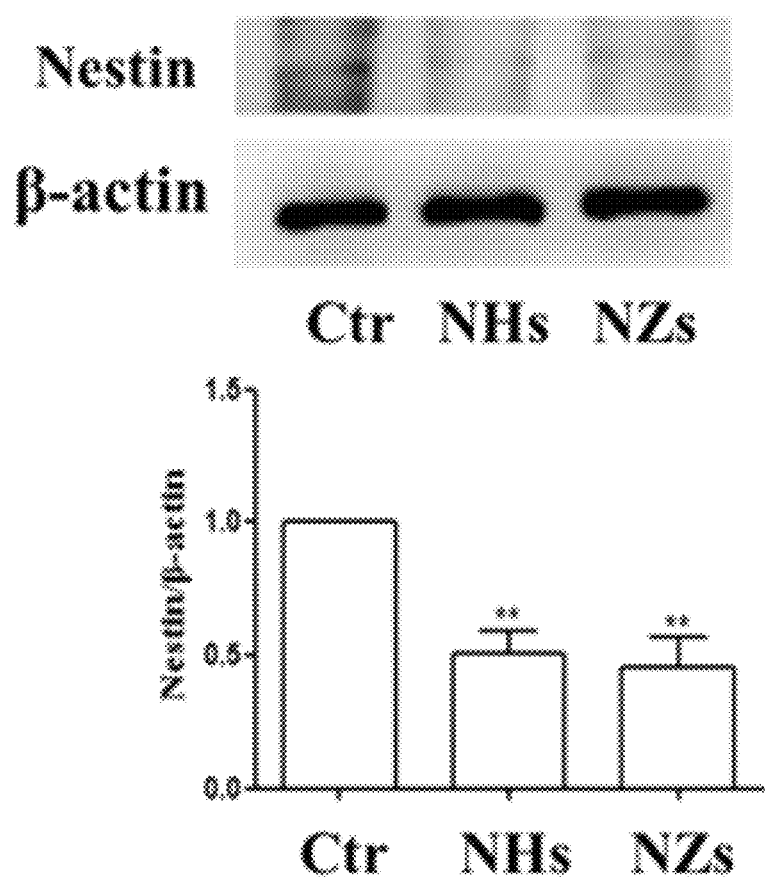
FIG. 10d shows western blot analysis of Nestin protein expression of NSC cultured on $TiO_x$ ECnMs in a shape of the helix (NHs) or zigzag (NZs) on day 4. *p<0.05, **p<0.01 compared with the control group.
Figure 10E:
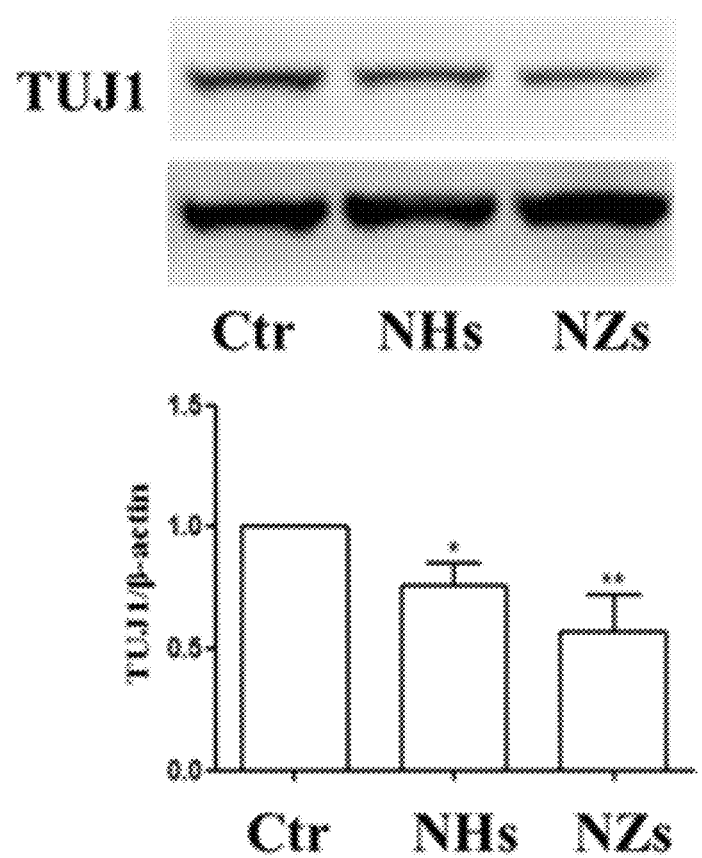
FIG. 10e shows western blot analysis of TUJ1 protein expression in NSC cultured on $TiO_x$ ECnMs in a shape of the helix (NHs) or zigzag (NZs) on day 7. *p<0.05, **p<0.01 compared with the control group.
Figure 10F:
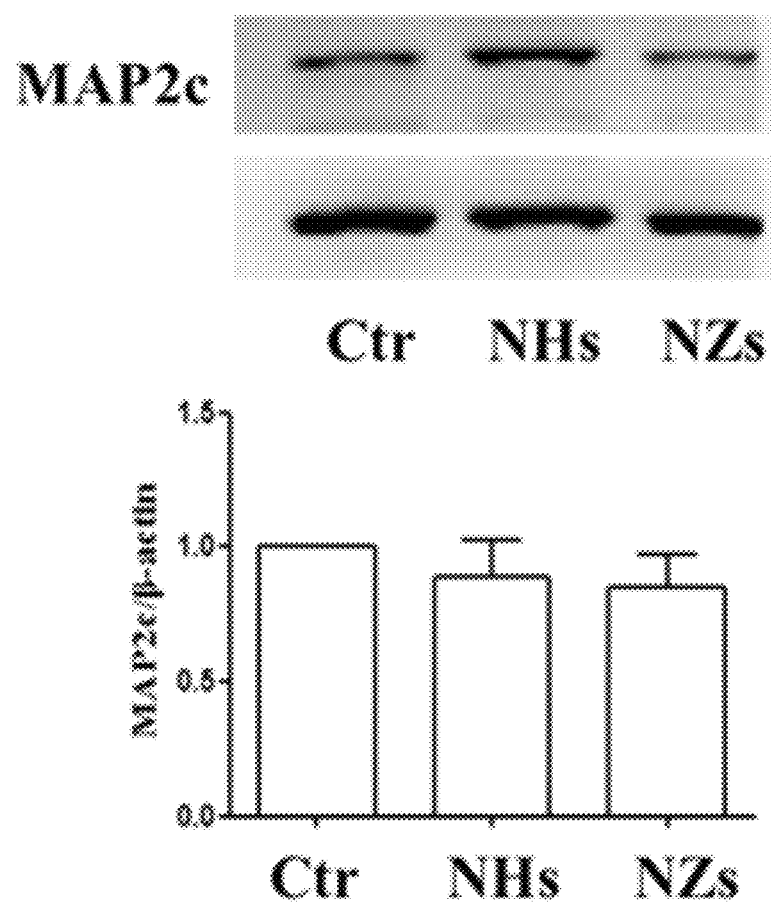
FIG. 10f shows western blot analysis of MAP2c protein expression in NSC cultured on $TiO_x$ ECnMs in a shape of the helix (NHs) or zigzag (NZs) on day 7. *p<0.05, **p<0.01 compared with the control group.

Formation of neurospheres is the first step to induce cell differentiation and neuronal cell maturation, which are crucial for neuro-repair and cell replacement therapy to treat diseases in the brain. Quick cell maturation is favored for transplantation, because it can shorten the time window to put NSCs in culture, a procedure with high medical and contamination risk. To demonstrate the NSC differentiation on the sculptured ECnMs, western blot and immunocytochemistry are performed (FIGS. 10a-10c, 7a, 8a and 9a). Western blot analysis shows that compared to the control group, on SiO$_2$ ECnMs, the expression of Nestin protein, a marker of NSCs, decreases on day 4 (FIG. 10a), and the expression of TUJ1 and MAP2c proteins markedly increase on day 7 (FIGS. 10b, 10c). TUJ1 is an important protein marker of maturing neurons, and the TUJ1 immunostaing reveals clearly the maturation of neuronal cell morphology with clear perikaryon and neurite outgrowths. MAP2 is an exclusive dendritic protein in neurons. The smallest isoform of MAP2, MAP2c, is known to be involved in synaptogenesis, which is down regulated in the later stages of neuronal development. A higher level of TUJ1 proteins is found on the SiO$_2$ NZs than SiO$_2$ NHs, while more MAP2c expression is observed on the SiO$_2$ NHs than SiO$_2$ NZs. As MAP2c is an early neuronal marker and its expression decreases in mature neurons, it is shown that NSC differentiation occurs earlier on SiO$_2$ NZs than on SiO$_2$ NHs. The immunocytochemistry results are in a well agreement with the western blot results (FIGS. 7a, 8a and 9a). It is illustrated that, without any chemical GF, the SiO$_2$ ECnMs effectively induces the growth of neurospheres and stimulate the differentiation of NSC to neurons. The SiO$_2$ NZs exhibits neuronal cell maturation faster than the SiO$_2$ NHs. No chemical GF is used, so that only the effects of the physiological cues, topography and stiffness of different structure of SiO$_2$ ECnMs on NSC differentiation are considered. The interaction of the spreading neurons and the lower portion of the

TABLE 1

Summary of the left-handed NHs and NZs of the present invention, made of SiO$_2$ or TiO$_x$: height (H), pitch (P), number of pitch (n), and wire diameter (d) in the upper portion of the nanostructure distal to the substrate on which the nanostructure is deposited. For each sample, multiple (not less than 10) measurements are taken to evaluate algebraic average value and standard deviation.

| ECnMs | H (nm) | P (nm) | n | d (nm) |
|---|---|---|---|---|
| SiO$_2$ NHs | 538 ± 4 | 241 ± 2 | 2 | 48 ± 2 |
| SiO$_2$ NZs | 553 ± 3 | 165 ± 2 | 3 | 46 ± 3 |
| TiO$_x$ NHs | 480 ± 3 | 213 ± 4 | 2 | 47 ± 3 |
| TiO$_x$ NZs | 365 ± 7 | 138 ± 4 | 3 | 42 ± 6 |

Figure 12A:
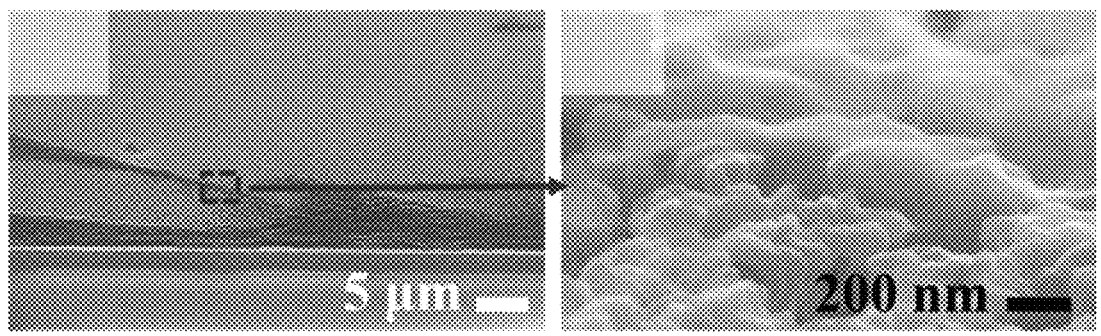
FIG. 12a shows cross-sectional SEM images of NSC differentiation on the $SiO_2$ NHs ECnMs, on day 7.
Figure 12B:
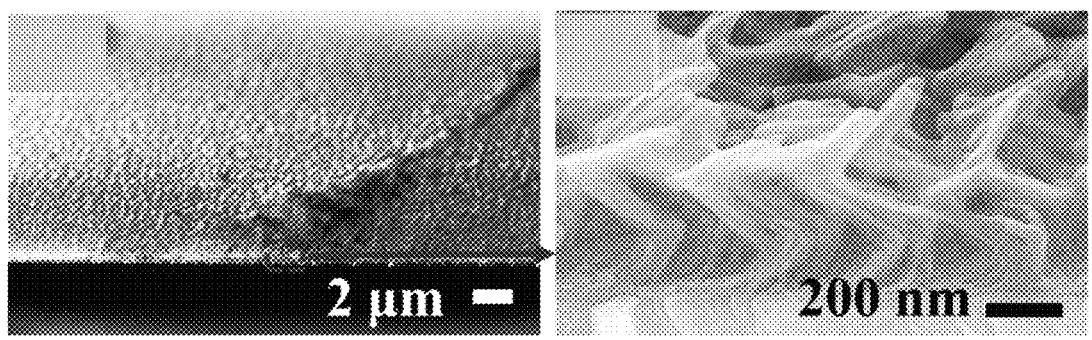
FIG. 12b shows cross-sectional SEM images of NSC differentiation on the $SiO_2$ NZs ECnMs, on day 7.

ECnM proximal to the substrate on which the ECnM is deposited was studied by SEM. The differentiated neuron cells strongly adhere to the $SiO_2$ NHs and NZs (FIGS. 12a-12b), consistent with the previous report that the cellular interaction with the two-dimensional ECMs happens on the base of the cells. The fibrillar focal contacts are formed to an extent that the spreading neuronal cells strongly wrap the upper portion of the $SiO_2$ ECnMs, indicating that the differentiated neuron cells can perceive different topographies of the NHs and NZs. The topography cues, including contact depth, geometrical profile of contacts, and cell adhesion area, will play an essential role in the NSC differentiation. The comparison of the $SiO_2$ NHs and NZs is made, with respect to the three topography cues. The contact depth, which is the distance NSCs make contact with the ECnMs, is roughly the half pitch of the NHs (i.e., ~120 nm, FIG. 12a) and the pitch of the NZs (i.e., ~160 nm, FIG. 12b) proximal to NSCs. It was reported that human mesenchymal stem cells on the 100-nm-depth patterns develop a higher level of cellular organization than on the 10-nm-depth patterns, eventually resulting in a differentiation into the osteoblast lineage. It is indicated that large contact depth, which the $SiO_2$ NZs have, facilitate the NSC differentiation. For the geometrical profile, the NHs have a helical profile and the NZs have a profile of tilted rod with a surface smoother than the NHs (FIG. 1b versus 1a). Furthermore, the NZ arrays appear to have disorder grooves at the neuron/ECnM contacts (inset of FIG. 2b), which is not observed on the helical ECnMs (inset of FIG. 2a). It is reported that the NSC differentiation is favored on nano-patterned substrates with grooves, consistent with the present invention. It may be ascribed to that more surface grooves can enhance focal adhesion and allow more physical contacts between the growing cell bodies and the ECnMs, especially when the neuritis expands to be embedded into the spaces in-between the zigzag nanostructures. To calculate the cell adhesion area, it is necessary to measure the surface density of the nanostructures in the ECnMs, which is prohibited by the blurry top-down view SEM images of the $SiO_2$ ECnMs owing to their low electric conductivity. Furthermore, stiffness of the ECnMs controls the eventual fate of the cell type, which are discussed below.

Figure 1F:
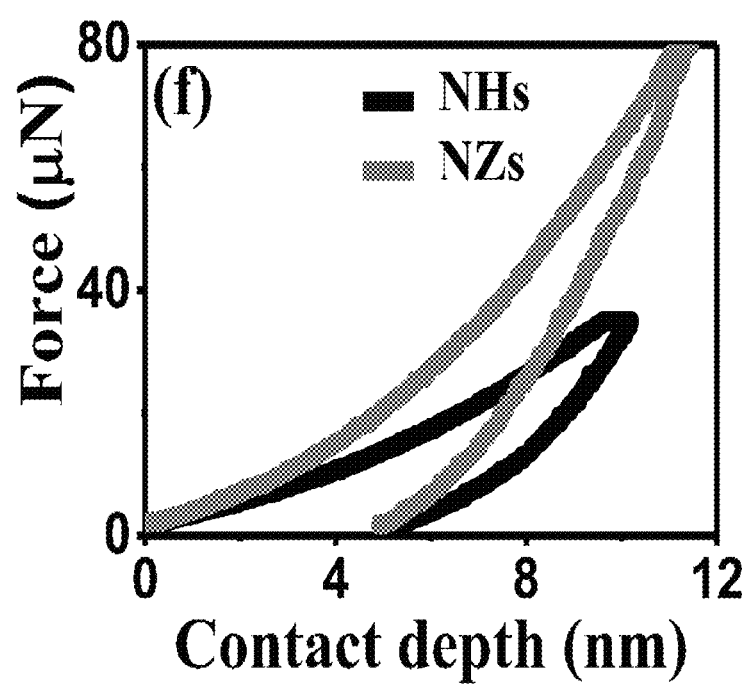
FIG. 1f shows nanoindentation plots of NHs and NZs of $SiO_2$ECnM by GLAD.
Figure 13A:
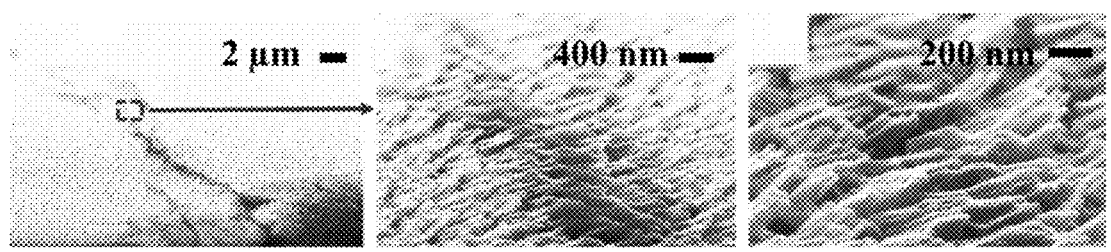
FIG. 13a shows cross-sectional SEM images of NSC differentiation on the $TiO_x$ NZs ECnMs, on day 7.
Figure 13B:
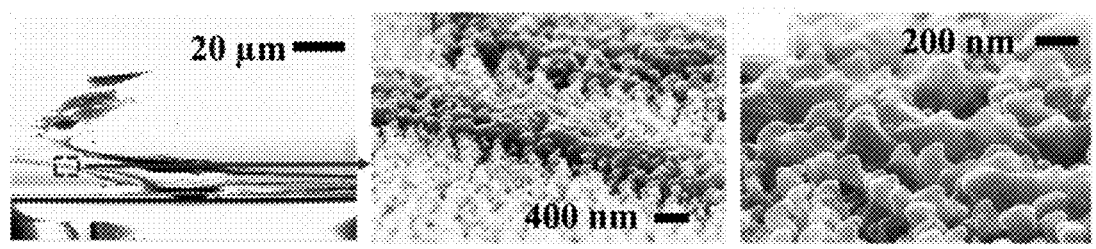
FIG. 13b shows cross-sectional SEM images of NSC differentiation on the $TiO_x$ NHs ECnMs, on day 7.
Figure 14:
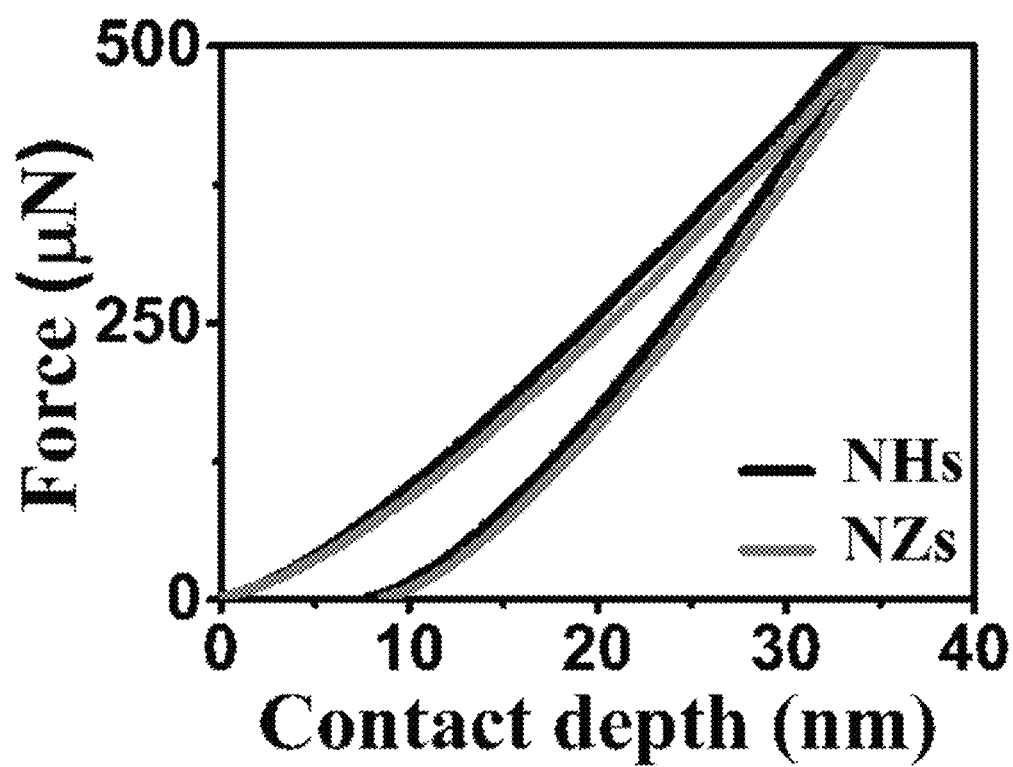
FIG. 14 shows nanoindentation plots of the $TiO_x$ ECnMs, in a shape of the helix or zigzag.

Although the $TiO_x$ ECnMs can induce the NSC proliferation and neurosphere growth (FIGS. 3b and 6), they tend not to promote the differentiation into neuron commitment, compared to the control group (FIGS. 7b, 10d-10f). The differentiated neuron cells adhere to the $TiO_x$ ECnMs in a way analogous to those on the $SiO_2$ ECnMs (FIG. 13a-13b). Given a shape of the helix or zigzag, the TiOx ECnMs have a nanostructure similar to that of the $SiO_2$ ECnMs (Table 1). It is indicated that the morphology cues could hardly account for a material-caused difference in the NSC differentiation on the inorganic ECnMs. The difference in degree of NSC differentiation attributes to the stiffness of the ECnMs, which is evaluated by nanoindentation. The $SiO_2$NHs have a stiffness of 12.6±1.8 µN/nm, lower than 19.7±2.3 µN/nm for the $SiO_2$ NZs (FIG. 1f). The $TiO_x$ ECnMs have a shape-independent stiffness of ~26 µN/nm (FIG. 14), higher than the $SiO_2$ ECnMs. As discovered by the inventors, the stiffness of ECMs have a complex effect on cell commitment. For example, soft ECMs (below 10 µN/nm) favor the differentiation to pluripotent stem cells, and intermediate stiffness gels greatly favor the neuron commitment. A biphasic response for mesenchymal stem cell differentiation is observed to have the maximum level of osteogenesis at intermediate stiffness, which could account for the phenomena observed in this work. In a intermediate stiffness between 10-30 µN/nm, the neuron commitment is the most favored, corresponding to intermediate stiffness of ~20 µN/nm for $SiO_2$ NZs. The $SiO_2$ NHs are too soft to strongly induce the neuron commitment. The TiOx ECnMs have such a high stiffness to prohibit the NSC differentiation; hence, $TiO_2$ isn't recommended for the GF-free NSC differentiation.

Without use of chemical GF, the $SiO_2$ ECnMs sculptured in the helix and zigzag by GLAD are employed to proliferate NSCs to form neurospheres and differentiate to neuron commitment in vitro. To the inventors' best knowledge, this is the first report on the realization of proliferation and differentiation of NSCs induced by ECnMs without chemical GF. The GF-free proliferation of NSCs tends to be faster than the GF-induced NSC growth. The sculptured shape has little effect on the NSC proliferation, but the zigzag structure is favored for the differentiation to neurons. Compared to the helix, the zigzag topography provides a larger contact depth and a large amount of grooves that lack in the helical to strongly enhance cell adhesion, and has an intermediate stiffness suitable for the neuron commitment. Although the sculptured ECnMs made of $TiO_x$ (0.33≤x≤2) can proliferate the growth of NSCs, they are too stiff to differentiate NSCs to neurons.

An embodiment of the present invention provides some profound impacts on the NSC proliferation and differentiation. First, the GF-free growth and differentiation of NSCs of the present invention significantly minimizes the risk of generating cancer cells in stem cell therapies. Second, the GLAD technique enables one to flexibly engineer material and structure of the sculptured ECnMs, opening a door to tailor cell fate by controlling the physiological cues of topography and stiffness of the ECnMs. Third, the GLAD technique offers a one-step-process production of the sculptured ECnMs in a large area (e.g., on a 4-inch wafer) with uniform structures. It paves the way to differentiate NSCs to the designable cell commitment with sufficient amount of differentiated cells, which is of urgent clinical demand for stem cell therapies.

Materials and Methodology

Nano-Matrixes

Inorganic nano-matrixes are deposited on surfaces by glancing angle deposition (GLAD), a special technique of physical vapor deposition. The deposition is operated at an incident angle of over 80 degree with respect to the substrate's surface normal, to generate the nano-matrix composed of an array of nanopillars of helices or zigzags. The materials of the nanopillars are those that can be physically evaporated, including, but not only limited to, dielectric materials (such as $SiO_x$ (FIGS. 1a-1f), $TiO_x$ (FIGS. 2a-2d), $FeO_xO_y$, $Ni_xO_y$, ITO), noble metals (such as Au, Ag), transition metals (Fe, Ni, Co), as well as their alloys and composites. The shape of the nanopillars is sculptured by controlling substrate rotation, including, but not only limited to, helices (FIG. 1a; FIGS. 2a and 2c), zigzag (FIG. 1b; FIGS. 2b and 2d), vertical posts, square spirals, and the combination of these structures in three-dimensional pattern. The nano-matrixes can be deposited on a wide range of substrates, including, but not only limited to, transparent (i.e., glasses), opaque (i.e. silicon wafers), electrically conductive (i.e., metals, ITO, ITO-coated glasses), and flexible (i.e., polymers) substrates.

GLAD of NHs and NZs:

In a custom-built physical vapor deposition system (Jun-Sun Tech Co. Ltd., Taiwan) with a high vacuum of $10^{-7}$-$10^{-6}$ Torr, $SiO_2$ (99.99%, Kurt J. Lesker company) and $TiO_2$ (99.9%, Kurt J. Lesker company) are evaporated at a rate of ~0.3 nm/s as monitored by a quartz crystal microbalance (QCM) located in the vicinity of a sample, using an electron-beam accelerating voltage of 8.0 kV and emission current of 83-87 mA. $SiO_2$ and $TiO_2$ are deposited at a deposition angle ($\alpha$) of 87° and 86° with respect to the substrate's surface normal, respectively. The samples are deposited on ITO glasses (Xin Yan Technology Ltd.) and Si wafers (Semiconductor Wafer, Inc.), and the substrate temperature is controlled at room temperature using an ethanol/water cooling system. To produce left/right-handed NHs, the substrate is rotated counterclockwise/clockwise at a rate $R_r$ (in units of degree per second, or °/s) given by $$R_r = 360 R_d / P \tag{S1}$$

where $R_d$ is the deposition rate on the substrate surface calibrated as 0.28 nm/s for $SiO_2$ at $\alpha$ of 87° and 0.12 nm/s for $TiO_2$ at $\alpha$ of 86°. P is the helical pitch, as-designed to be ~200 nm. To produce the NZs, the substrate is stepped back and forth in 180° intervals, during which tilted nanorods are deposited with a given length (i.e., zigzag pitch). The structures of the ECnMs are summarized in Table 1.

Material Characterization:

The as-deposited samples are mechanically split, leaving the freshly exposed surfaces for the characterization of scanning electron microscopy (SEM, Oxford, LEO 1530). The NHs and NZs are scratched off the substrates and well dispersed in ethanol via ultra-sonication for 5 minutes. Several drops of the mixture are applied to a lacey carbon film on a grid structure (Electron Microscopy Sciences). The grid is dried in ambient and inspected by transmission electron microscopy (TEM, Tecnai G2 20 STWIN). Without post-deposition treatment, the samples are characterized by X-ray diffraction (XRD, Bruker, nonmonochromated Cu K$\alpha$ x-ray with wavelength of 0.15418 nm, Advance D8 multi-purpose x-ray diffractometer), X-ray photoelectron spectroscopy (XPS, Sengyang SKL-12, non-monochromatic Mg K$\alpha$ radiation of 1253.6 eV, at a current of 15 mA, voltage of 10 kV and takeoff angle (between the sample and detector) of 90°, and in a vacuum of $\sim 2 \times 10^{-9}$ mbar), and nanoindentation (Nano Indenter XP, with a spherical tip having a 100 μm of radius of curvature).

Neural Stem Cell Isolation and Cell Culture

Rats (Springe Dawley) are purchased from the Chinese University of Hong Kong. NSCs are dissected from SVZ of P1 to P2 rats, and cultured at a cell density of $2 \times 10^5$ cells per well in 24-well plate and $1.0 \times 10^6$ cells per well in 6-well plate in NBM (Gibco) with 10% FBS (Gibco), 1% PSN (Gibco) and 2% B27 Supplement (Gibco). After 4-day and 7-day incubation at 37° C. in 5% $CO_2$ on the inorganic ECnMs, the localization, proliferation, levels of specific proteins and neurospheres are analyzed.

Cytotoxicity Assay:

NSCs are cultured on glass plates as the control group, and on the ECnMs in 4-well plates in 1 ml complete medium per well, followed by the incubation for 4 and 7 days. The MTT assay is performed at day 4 and 7. MTT solution is added and placed into an incubator at 37° C. for 4 hours in dark. Then DMSO is added in the MTT solution to dissolve the dark purple crystals. The optical density of the solution is measured by a spectrophotometer at a wavelength of 570 nm.

Immunocytochemistry Assay:

NSCs in cultures are first stained with nuclear stain, DAPI (1 μg/ml) in 100% methanol for 15 minutes in dark in the incubator at 37° C., without irradiation. Then the cells are then rinsed (1×60% methanol) and are then fixed with 4% paraformaldehyde (PFA) for 30 minutes at room temperature in dark. The cells are then further incubated with specific primary antibody solutions in PBS with Triton and normal goat serum overnight, at 4° C. in dark. The cells are rinsed with PBS and then incubated with specific secondary antibody solutions in PBS for 3 hours at room temperature. After rinsed with PBS, the cells are mounted with fluorescence mounting medium (Dako). Immunoreactivity for the cells is imaged by confocal microscope (FluoView FV1000, Olympus).

Western Blotting Analysis:

Western blotting is employed to compare the levels of Nestin, TUJ1 and MAP2c proteins in NSCs growing on the ECnMs. Proteins are extracted in protein extraction reagent (Novagen) supplemented with Protease Inhibitor Cocktail (Calbiochem). Protein concentration is measured using the Bio-Rad protein assay kit (Bio-Rad). Total proteins (30 μg) per sample are separated on 10% SDS-polyacrylamide gels and transferred to a polyvinylidene difluoride (PVDF) membrane. The Membrane is probed with anti-Nestin antibodies (Millipore, 1:1000), anti-TUJ1 antibodies (Millipore, 1:1000), or anti-MAP2c antibodies (Millipore, 1:1000), followed by an incubation with secondary antibody conjugated with HR. β-actin antibodies (Sigma, 1:5000) is used as a reference to assess the relative amounts of proteins loaded per lane. Images of bands are captured using gel documentation system (Bio-Rad).

Statistical Analysis:

Quantitative results are expressed as mean±Data of NSC proliferation and differentiation are analyzed by one-way analysis of variance in SPSS, and multiple measurements are operated to evaluate algebraic average value and standard deviation. All analyses are made using GraphPad Prism 5.0. Statistical significance was defined as $p<0.05$.

Lysis of Cells in Culture

In cell cultures, all medium from the culture is removed and the cells are rinsed with ice-cold phosphate-buffered saline (3×PBS). Lysis buffer is added to each well and cells are scrapped by rubber scrappers on ice. The cell lysates are then collected and centrifuged at 11,000 g for 30 min at 4° C. The supernatants are collected in an Eppendorf tube for subsequence experiments.

Determination of Protein Concentrations

Prior to gel electrophoresis, protein concentrations are measured (Bio-Rad protein assay kit). The samples are diluted 10 folds with MiliQ water and 5 ul of samples are loaded to 96-well plate with adding of 25 ul of Reagent A and 200 ul Reagent B. The plate is then incubated in dark for 30 min at room temperature. Total protein concentration was measured as the optical density at 750 nm by a spectrophotometer.

Gel Electrophoresis (SDS-PAGE)

Equal concentrations of protein from each experimental group are employed. The protein samples are first denatured at 100° C. for 5 min with SDS before gel electrophoresis. Samples are mixed with electrophoresis buffer and then are loaded in gel. Electrophoresis is started using 30V for about 30 minutes and then with 70V for about 3 hours at room temperature.

Protein Blotting

After the completion of separation of proteins using gel electrophoresis, the proteins on the gel are transferred to polyvinylidene difluoride membranes overnight at 15V in transfer buffer.

Western Blotting

After incubation with specific antibodies, the membranes are washed with tris-buffered saline with tween 20 (TBST; 2×10 min), then with TBS (1×10 min). Protein bands are visualized with chemiluminescence detection reagent WESTSAVE Up. Images of bands are captured using gel documentation system (Bio-Rad).

There are four main features in this invention:

I. Nano-Matrixes are Non-Toxic to Cells in Culture

Figure 4:
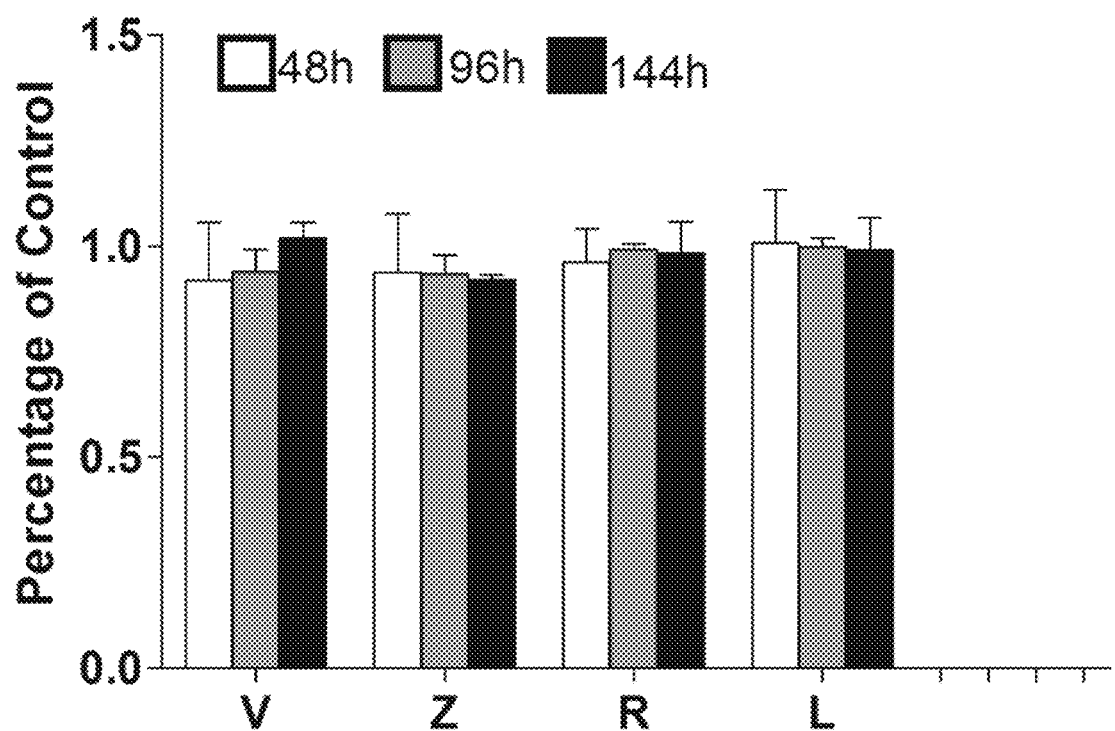
FIG. 4 shows the cell viability of neuronal cell SH-SY5Y on different nano-matrix.

Results of the MTT assays have shown that nano-matrixes of TiOx and $SiO_2$ do not affect the cell viability of both NSC (FIGS. 3a and 3b) and SY-SH5Y cells (FIG. 4). The nano-matrixes are therefore non-toxic.

II. Physical Substrates of the Nano-Matrixes can Promote Cell Proliferation of Neural Stem Cells into Neurospheres The presented data indicate that no additional growth factors (GF) or other chemical factor is required in inducing the growth of neurospheres from NSCs (FIG. 5 and FIG. 6). In conventional NSCs culture method, "neurosphere assay", differentiated cells die within a few days and therefore a small group of undifferentiated cells can proliferate actively in respond to epidermal growth factors (EGF) and basic fibroblastic growth factor (bFGF) to form into neurosphere. In conventional NSCs culturing, the growth of cells is highly dependent on the use of growth factors. If no growth factors are added, the cells will die. However, growth factors are very potent in regulating cell-signaling pathways. If high amount of growth factors is used to induce the differentiation of stem cells in vitro, it poses a risk of developing cancer cells in vitro or tumors in vivo after transplantation. For example, fibroblast growth factor (FGF) signaling, that is crucial for proliferation, survival and migration, has been shown to play an oncogenic role in many cancers. Moreover, vascular epidermal growth factors (VEGF), an inducer of angiogenesis, and that deregulated insulin growth factor (IGF) are related to the initiation and progression of cancer.

The inventors show in the first time achieving cell proliferation and differentiation on nano-matrixes without the addition of chemical growth factors (FIG. 5 and FIG. 6). As early as at day 4, clear neurospheres with diameters around 50 µm are achieved. The proliferation of NSCs that grow on nano-matrixes is found to be much enhanced than those found in the controls (FIG. 5 and FIG. 6).

The present nano-matrix comprises material selected from $SiO_2$ or TiOx. The present nano-matrix can initiate cell proliferation for the formation of the neurospheres. $SiO_2$ has much stronger effect in promoting the cell proliferation in formation of neurospheres (FIG. 5). From those different $SiO_2$ structures studies, $SiO_2$ Zigzag structures are found to be the best structure in generation of neurospheres (FIG. 5). TiOx Zigzag structures are in general found to be comparable to the SiOx structures, whereas TiOx Spiral structures are less effective in causing cell proliferation (FIG. 6). These differences in cell proliferation attributes at least partly to the differences in stiffness of the materials.

III. Maturation of Neurons from Neural Stem Cells can be Accelerated by the Nano-Matrixes Formation of neurospheres is the first step for cell differentiation and neuronal cell maturation. These are crucial steps for neuro-repair and cell replacement therapy for diseases in the brain. Quicker cell maturation can result in quicker transplantation and can shorten the time window for putting NSCs in culture, a procedure with high medical and contamination risks for patients. The results shows that a swift neuronal cell maturation can be achieved by using the present nano-matrixes without using chemical growth factors (FIGS. 7a-7b, 8a-8b, 9a-9b).

Figure 7B:
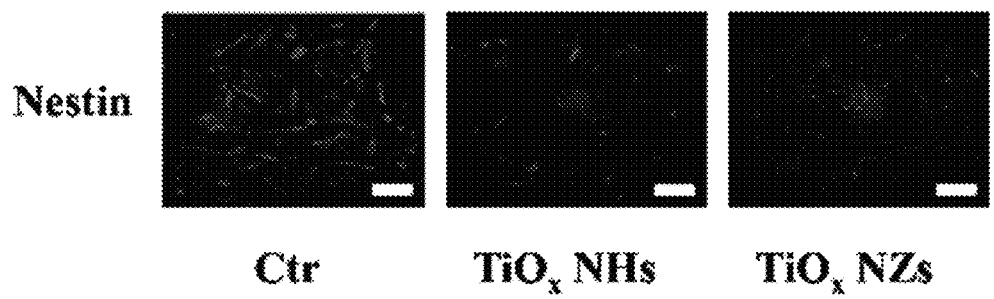
FIG. 7b shows fluorescence images of Nestin in NSC cultured on $TiO_x$ ECnMs in a shape of the helix (NHs) or zigzag (NZs). Scale bar: 50 μm.

Both $SiO_2$ and TiOx nano-matrixes of the present invention promote the expression of nestin, a fibrillary protein that is related to stemness of NSCs and is a marker for NSCs. These results at day 4, NSCs are activated by the nano-matrixes to promote growth and to start the cell maturation processes (FIGS. 7a-7b).

Figure 8B:
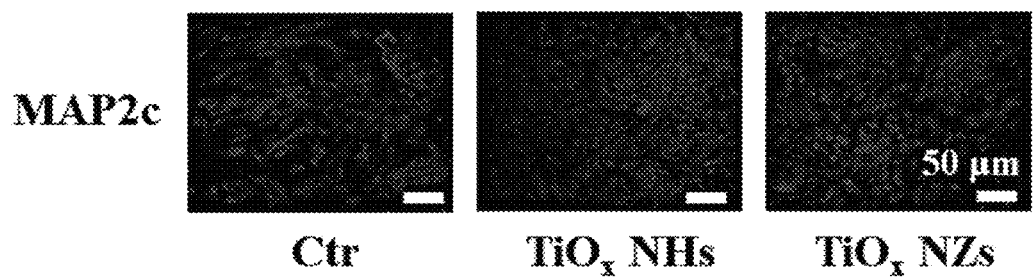
FIG. 8b shows fluorescence images of MAP2c in NSC cultured on the $TiO_x$ ECnMs in a shape of the helix (NHs) or zigzag (NZs). Scale bar: 50 μm.

There are also continuous rise of MAP-2 protein levels in NSCs growing on the nano-matrixes (FIGS. 8a-8b and FIG. 10c). MAP-2 is an exclusive dendritic protein in neurons. These indicate there are increases in synthesis of dendritic proteins with the contacts on the nano-matrixes. $SiO_2$ structures are found to perform better in promoting the growth of dendrites.

Figure 9B:
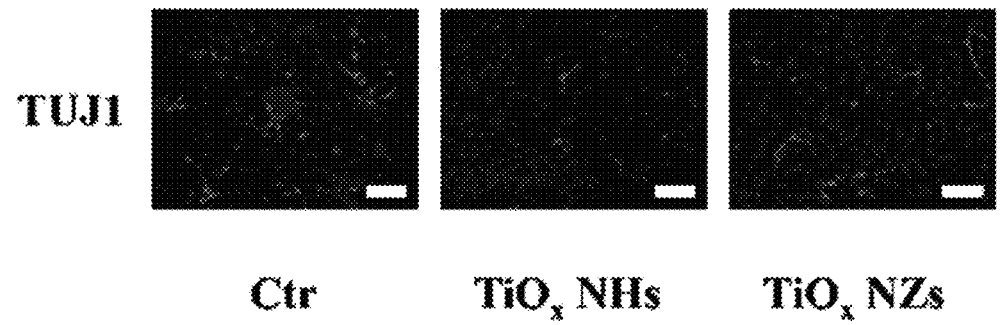
FIG. 9b shows fluorescence images of TUJ1 in NSC cultured on the $TiO_x$ ECnMs in a shape of the helix (NHs) or zigzag (NZs). Scale bar: 50 μm.

Similar to MAP-2 proteins, TUJ-1 is also an important protein marker for maturing neurons. TUJ-1 immunostaing can reveal clearly the maturation of neuronal cell morphology with clear perikaryon and neurite outgrowths. In terms of cell maturation towards neurons, among the two materials tested, $SiO_2$ is a better material for achieving this purpose (FIG. 9a). A much higher number of TUJ-1-immunpositive maturing neurons are found after incubating on $SiO_2$ ZigZag nano-matrixes (FIG. 9b). These results are also strongly supported by Western blotting analysis (FIG. 10b). Similar to the cell proliferation effects, the differences in effectiveness causing neuronal cell maturation may also be at least partly due to the stiffness of the materials.

IV. Nanotopography is Crucial for Cell Differentiation

Nanostructure, the shapes, of the material on the matrixes is a key factor that affects the proliferation and differentiation of NSCs. More and more evidences have shown that the cells can "fell" the topographies of matrixes from nanometer to micrometer scale, as the topography can induce pronounced changes in the pattern of focal adhesion structure, influencing the cytoskeleton and consequently gene expression. As a result, the topographical information could mediate stem cell differentiation and proliferation. The cells preferentially differentiate into neurons on top of one of the matrixes. In general, zigzag structures are found to be more effective than the other structures in promotion of cell proliferation and cell differentiation of NSCs (FIGS. 5 to 9b). These observations maybe due to the fact that there are more "grooves" and nanospaces in the zigzag structures that can allow more physical contacts between the growing cell bodies and neurites of the NSCs especially when the neurites are extending then embedded into the space in between the zigzag structures.

Pure mechanical support is provided to cells and material itself shows no effects on cells viability. In natural environment, cells respond to its surroundings by interacting with extracellular matrix (ECM) in a nanometer scale. Topography of extracellular can influence cell attachment, migration, proliferation as well as differentiation. As a result, an increasing attention has been focused on the nanotopography for its resemblance to the in vitro environment.

CONCLUSION

The present invention provides a "growth factor free" physical nanostructure that promotes cell proliferation, cell differentiation and maturation of NSCs in culture. The invention will form an important step in achieving safe and cost-effective mean of cell maturation process in future possible clinical applications of cell processing technology for cell therapies of diseases in the brain.

The invention claimed is:
1. A nanostructure comprising a plurality of nanohelices or nanozigzags, wherein the plurality of nanohelices or nanozigzags are made of $SiO_2$ or $TiO_x$, wherein x is in the range of $0.33 \leq x \leq 2$, wherein the nanohelices made of $SiO_2$ has a stiffness of 12.6±1.8 μN/nm;

wherein the nanozigzags made of $SiO_2$ has a stiffness of 19.7±2.3 μN/nm and an intermediate stiffness greatly favoring neuron commitment has an intermediate stiffness between 10-30 μN/nm;

wherein the plurality of nanohelices or nanozigzags made of $TiO_x$ has a shape independent stiffness of no more than 26 μN/nm.

2. The nanostructure according to claim 1, wherein the nanostructure comprises a plurality of nanohelices, length of each of the nanohelix is at least 540 nm and each nanohelix comprises at least two pitches and having a pitch of at least 240 nm.

3. The nanostructure according to claim 1, wherein the nanostructure comprises a plurality of nanozigzags, length of each of the nanozigzag is at least 550 nm and each nanozigzag comprises at least three pitches and having a pitch of at least 165 nm.

4. The nanostructure according to claim 1, wherein the nanostructure comprises a plurality of left-handed oriented nanohelices.

5. The nanostructure according to claim 1, wherein the nanostructure comprises a plurality of right-handed oriented nanohelices.

6. The nanostructure of claim 1, wherein the nanostructure is manufactured by GLAD technique.

7. A method for inducing proliferation of stem cells comprises culturing the stem cells on the nanostructure of claim 1 in the absence of chemical growth factors.

8. The method according to claim 7, wherein said stem cells are neural stem cells.

9. The method according to claim 8, wherein the nanostructure comprises a plurality of nanohelices, length of each of nanohelix is at least 540 nm and each nanohelix comprises at least two pitches and having pitch of at least 240 nm.

10. The method according to claim 8, wherein the nanostructure comprises a plurality of nanozigzags, length of each of nanozigzag is at least 550 nm and each nanozigzag comprises at least three pitches and having a pitch of at least 165 nm.

11. A method of inducing proliferation and differentiation of stem cells comprises culturing the stem cells on nanostructure of claim 1, wherein the plurality of nanohelices or nanozigzags are made of $SiO_2$.

12. The method of claim 11, wherein the stem cells are neural stem cells.

* * * * *